(12) United States Patent
Cramer et al.

(10) Patent No.: US 11,578,316 B2
(45) Date of Patent: Feb. 14, 2023

(54) ACETOLACTATE DECARBOXYLASE VARIANTS HAVING IMPROVED SPECIFIC ACTIVITY

(71) Applicant: DuPont Biosciences APS, Copenhagen (DK)

(72) Inventors: Jacob Flyvholm Cramer, Brabrand (DK); Lene Kragh, Hojbjerg (DK)

(73) Assignee: DUPONT NUTRITION BIOSCIENCES APS, Kongens Lyngby (DK)

( * ) Notice: Subject to any disclaimer, the term of this patent is extended or adjusted under 35 U.S.C. 154(b) by 116 days.

(21) Appl. No.: 16/332,485

(22) PCT Filed: Sep. 12, 2017

(86) PCT No.: PCT/EP2017/072915
§ 371 (c)(1),
(2) Date: Mar. 12, 2019

(87) PCT Pub. No.: WO2018/050649
PCT Pub. Date: Mar. 22, 2018

(65) Prior Publication Data
US 2021/0301279 A1    Sep. 30, 2021

Related U.S. Application Data

(60) Provisional application No. 62/395,592, filed on Sep. 16, 2016.

(51) Int. Cl.
| | |
|---|---|
| *C12N 9/88* | (2006.01) |
| *C12H 1/00* | (2006.01) |
| *C12H 1/22* | (2006.01) |
| *C12N 1/20* | (2006.01) |
| *C12R 1/125* | (2006.01) |

(52) U.S. Cl.
CPC .............. *C12N 9/88* (2013.01); *C12H 1/006* (2013.01); *C12H 1/22* (2013.01); *C12N 1/20* (2013.01); *C12N 2500/22* (2013.01); *C12R 2001/125* (2021.05); *C12Y 401/01005* (2013.01)

(58) Field of Classification Search
None
See application file for complete search history.

(56) References Cited

U.S. PATENT DOCUMENTS

| | | |
|---|---|---|
| 5,246,853 A | 9/1993 | Clarkson et al. |
| 5,475,101 A | 12/1995 | Ward et al. |
| 5,605,793 A | 2/1997 | Stemmer |
| 5,811,238 A | 9/1998 | Stemmer et al. |
| 5,830,721 A | 11/1998 | Stemmer et al. |
| 5,837,458 A | 11/1998 | Minsull et al. |
| 5,874,276 A | 2/1999 | Fowler et al. |
| 6,022,725 A | 2/2000 | Fowler et al. |
| 6,268,328 B1 | 7/2001 | Mitchinson et al. |
| 2018/0171323 A1* | 6/2018 | Cramer .......... C12Y 401/01005 |

FOREIGN PATENT DOCUMENTS

| | | |
|---|---|---|
| DK | 149335 B | 5/1986 |
| EP | 0244234 B1 | 7/1993 |
| EP | 0238023 B1 | 12/1993 |
| EP | 0215594 B1 | 1/1995 |
| WO | 9206209 A1 | 4/1992 |
| WO | 9600787 A1 | 1/1996 |
| WO | 0214490 A2 | 2/2002 |
| WO | 2005001036 A2 | 1/2005 |
| WO | 2016191169 A2 | 12/2016 |
| WO | 2016191170 A2 | 12/2016 |

OTHER PUBLICATIONS

Marlow et al. ACS Chem. Biol. 2013, 8, 10, 2339-2344 (Year: 2013).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Yoshikuni et al. Curr Opin Chem Biol. Apr. 2007;11(2):233-9. (Year: 2007).*
Diderichsen et al. J Bacteriol. Aug. 1990;172(8):4315-21. (Year: 1990).*
Altschul et al., "Basic Local Alignment Search Tool", J. Mol. Biol. 215,1990, pp. 403-410.
Anagnostopoulos et al., "Requirements for Transformation in Bacillus Subtilis", J. Bacteriol.. Vol. 81,1961, pp. 741-746.
Ausubel et al., "Short Protocols in Molecular Biology", Fourth Edition, Wiley, 1987, 20 pages.
Bajar et al., "Identification of a fungal cutinase promoter that is inducible by a plant signal via a phosphorylated trans-acting factor", Proc. Natl. Acad. Sci. USA, vol. 88, Sep. 1991, pp. 8208-8212.
Campbell et al., "Improved transformation efficiency of Aspergillus niger using the homologous niaD gene for nitrate reductase", Curr Genet, vol. 16, 1989, pp. 53-56.
Dao et al., "Penicillopepsin-JT2, a reconbinant enzyme from Penicillum janthinellum and the contribution of a hdrogen bond in subsite S2to kcat", Protein Scient, vol. 9, 2000, pp. 991-1001.
Chenna et al., "Multiple sequence alignment with the Clustal series of programs", Nucleic Acids Research, vol. 31, No. 13, 2003, pp. 3497-3500.
Coombs; et al. "Site-Directed Mutagenesis and Protein Engineering", in Proteins: Analysis and Design, 1998, Academic Press, Inc., article pp. 259-311.
Emanuelsson et al., "Locating proteins in the cell using TargetP, SignalP, and related tools", Nat. Protoc, vol. 2, Feb. 2007, pp. 953-971.
Fromant et al., "Direct random mutagenesis of gene-sized DNA fragments using polymerase chain reaction", Anal Biochem., Volv 224(1), Jan. 1995, pp. 347-353.

(Continued)

*Primary Examiner* — Christian L Fronda

(57) ABSTRACT

Compositions and methods are provided comprising acetolactate decarboxylase (ALDC) enzyme variants having higher specific activity. Composition and method are provided where the ALDC variants are used in combination with metal ions to further increase stability and/or activity.

21 Claims, 3 Drawing Sheets

Specification includes a Sequence Listing.

(56) References Cited

OTHER PUBLICATIONS

Goedegebuur et al., "Cloning and relational analysis of 15 novel fungal endoglucanases from family 12 glycosyl hdrolase", Curr Geet, vol. 41, 2002, pp. 89-98.
Harkki et al., "Genetic engineering of Trichoderma to produce strains with novel cellulase profiles", Enzyme Microb. Technol vol. 13, Mar. 1991, pp. 227-233.
Harkki et al., "A Novel Fungal Expression System: Secretion of Active Calf Chymosin from the Filamentous Fungus Trichoderma Reesei", Biotechnology vol. 7, Jun. 1989, pp. 596-603.
Higgins et al., "Fast and sensitive multiple sequence alignments on a microcomputer", Cabios Communications, vol. 5, No. 2, 1989, pp. 151-153.
Innis et al., "Expression, blycosylation, and Secretion of an Aspergillus Glucoamylase by *Saccharaomyces cerevisiae*". Science, vol. 228, Apr. 5, 1985, pp. 21-26.
Lin-Goerke et al., "PCR-Baed Random Mutagenesis Using Manganese and Reduced dNTP Concentration", BioTechniques vol. 23, No. 3, 1997, 409-412.
Melnikov et al., "Random matagenesis by recombinational capture of PCR products in Bacillus subtilis and Acinetobacter calcoaceticus", Nucleic Acids Research, vol. 27, No. 4, 1999, pp. 1056-1062.
Nevalainen et al., "The Molecular Biology of Trichoderma and Its Application to the Express of Both Homologous and Heterologous Genes", Molecular Industrial Mycology, Eds. Leong and Berka, Marcel Dekker Inc., NY, 1992, pp. 129-148.
Nixon et al., "Assembly of an active enzyme by the linkage of two protein modules", Proc. Natl. Acad. Sci. USA, vol. 94, Feb. 1997, pp. 1069-1073.
Sheir-Neiss et al., "Characterization of the secreted cellulases of Trichoderma reesei wild type and mutants during controlled fermentations", Appl Microbiol Biotechnol, vol. 20, 1984, pp. 46-53.
Thompson et al., "Clustal W: Improving the Sensitivity of Progressive Multiple Sequence Alignment through Sequence Weighting, Position-Specific Gap Penalties and Weight Matrix Choice", Nucleic Acids Research, vol. 22, 1994, pp. 4673-4680.
Nard et al., "Use of Aspergillus overproducing mutants, cured for integrated plasmid, to overproduce heterologous proteins", Appl Microbiol Biotechnol, vol. 39, 1993, pp. 738-743.
Yelton et al., "Transformation of Aspergillus nidulans by using a trpC plasmid", Proc. Natl. Sci. USA, vol. 81, Mar. 1984-pp. 1470-1474.
International Preliminary Report on Patentability from PCT Application No. PCT/EP2017/072915 dated Mar. 19, 2019, 8 pages.
International Search Report and Written Opinion from PCT Application No. PCT/EP2017/072915 dated Nov. 9, 2017, 12 pages.

\* cited by examiner

ID NO: 3 or

```
                         SEQUENCE LISTING

<160> NUMBER OF SEQ ID NOS: 8

<210> SEQ ID NO 1
<211> LENGTH: 858
<212> TYPE: DNA
<213> ORGANISM: Brevibacillus brevis

<400> SEQUENCE: 1
atgaaaaaaa atatcatcac ttctatcaca tctctggctc tggttgccgg gctgtctttg      60
actgcttttg cagctacaac ggctactgta ccagcaccac ctgccaagca ggaatccaaa     120
cctgcggttg ccgctaatcc ggcaccaaaa aatgtactgt ttcaatactc aacgatcaat     180
gcactcatgc ttggacagtt tgaaggggac ttgactttga aagacctgaa gctgcgaggc     240
gatatggggc ttggtaccat caatgatctc gatggagaga tgattcagat gggtacaaaa     300
ttctaccaga tcgacagcac cggaaaatta tcggagctgc agaaagtgt gaaaactcca      360 tttgcggtta ctacacattt cgagccgaaa gaaaaaacta cattaaccaa tgtgcaagat     420
tacaatcaat taacaaaaat gcttgaggag aaatttgaaa acaagaacgt cttttatgcc     480
gtaaagctga ccggtaccct taagatggta aaggctagaa cagttccaaa acaaaccaga     540
ccttatccgc agctgactga agtaaccaaa aaacaatccg agtttgaatt taaaaatgtt     600
aagggaaccc tgattggctt ctatacgcca aattatgcag cagccctgaa tgttcccgga     660
ttccatctcc acttcatcac agaggataaa acaagtggcg gacacgtatt aaatctgcaa     720
tttgacaacg cgaatctgga aatttctccg atccatgagt ttgatgtaca attgccgcac     780
acagatgatt tgcccactc tgatctgaca caagttacta ctagccaagt acaccaagct      840
gagtcagaaa gaaaataa                                                  858

<210> SEQ ID NO 2
<211> LENGTH: 285
<212> TYPE: PRT
<213> ORGANISM: Brevibacillus brevis

<400> SEQUENCE: 2

Met Lys Lys Asn Ile Ile Thr Ser Ile Thr Ser Leu Ala Leu Val Ala
```

```
            1               5                  10                 15
         Gly Leu Ser Leu Thr Ala Phe Ala Ala Thr Thr Ala Thr Val Pro Ala
                    20                 25                 30

Pro Pro Ala Lys Gln Glu Ser Lys Pro Ala Val Ala Ala Asn Pro Ala
                    35                 40                 45

Pro Lys Asn Val Leu Phe Gln Tyr Ser Thr Ile Asn Ala Leu Met Leu
             50                 55                 60

Gly Gln Phe Glu Gly Asp Leu Thr Leu Lys Asp Leu Lys Leu Arg Gly
         65                 70                 75                 80

Asp Met Gly Leu Gly Thr Ile Asn Asp Leu Asp Gly Glu Met Ile Gln
                         85                 90                 95

Met Gly Thr Lys Phe Tyr Gln Ile Asp Ser Thr Gly Lys Leu Ser Glu
                        100                105                110

Leu Pro Glu Ser Val Lys Thr Pro Phe Ala Val Thr Thr His Phe Glu
                        115                120                125

Pro Lys Glu Lys Thr Thr Leu Thr Asn Val Gln Asp Tyr Asn Gln Leu
                    130                135                140

Thr Lys Met Leu Glu Glu Lys Phe Glu Asn Lys Asn Val Phe Tyr Ala
         145                150                155                160

Val Lys Leu Thr Gly Thr Phe Lys Met Val Lys Ala Arg Thr Val Pro
                        165                170                175

Lys Gln Thr Arg Pro Tyr Pro Gln Leu Thr Glu Val Thr Lys Lys Gln
                        180                185                190

Ser Glu Phe Glu Phe Lys Asn Val Lys Gly Thr Leu Ile Gly Phe Tyr
                        195                200                205

Thr Pro Asn Tyr Ala Ala Ala Leu Asn Val Pro Gly Phe His Leu His
                    210                215                220

Phe Ile Thr Glu Asp Lys Thr Ser Gly Gly His Val Leu Asn Leu Gln
         225                230                235                240

Phe Asp Asn Ala Asn Leu Glu Ile Ser Pro Ile His Glu Phe Asp Val
                        245                250                255

Gln Leu Pro His Thr Asp Asp Phe Ala His Ser Asp Leu Thr Gln Val
                        260                265                270

Thr Thr Ser Gln Val His Gln Ala Glu Ser Glu Arg Lys
                    275                280                285

<210> SEQ ID NO 3
<211> LENGTH: 261
<212> TYPE: PRT
<213> ORGANISM: Brevibacillus brevis

<400> SEQUENCE: 3

Ala Thr Thr Ala Thr Val Pro Ala Pro Ala Lys Gln Glu Ser Lys
         1               5                  10                 15

Pro Ala Val Ala Ala Asn Pro Ala Pro Lys Asn Val Leu Phe Gln Tyr
                     20                 25                 30

Ser Thr Ile Asn Ala Leu Met Leu Gly Gln Phe Glu Gly Asp Leu Thr
                     35                 40                 45

Leu Lys Asp Leu Lys Leu Arg Gly Asp Met Gly Leu Gly Thr Ile Asn
             50                 55                 60

Asp Leu Asp Gly Glu Met Ile Gln Met Gly Thr Lys Phe Tyr Gln Ile
         65                 70                 75                 80

Asp Ser Thr Gly Lys Leu Ser Glu Leu Pro Glu Ser Val Lys Thr Pro
                         85                 90                 95
```

```
Phe Ala Val Thr Thr His Phe Glu Pro Lys Glu Lys Thr Thr Leu Thr
                100                 105                 110

Asn Val Gln Asp Tyr Asn Gln Leu Thr Lys Met Leu Glu Glu Lys Phe
            115                 120                 125

Glu Asn Lys Asn Val Phe Tyr Ala Val Lys Leu Thr Gly Thr Phe Lys
        130                 135                 140

Met Val Lys Ala Arg Thr Val Pro Lys Gln Thr Arg Pro Tyr Pro Gln
145                 150                 155                 160

Leu Thr Glu Val Thr Lys Lys Gln Ser Glu Phe Glu Phe Lys Asn Val
                165                 170                 175

Lys Gly Thr Leu Ile Gly Phe Tyr Thr Pro Asn Tyr Ala Ala Ala Leu
            180                 185                 190

Asn Val Pro Gly Phe His Leu His Phe Ile Thr Glu Asp Lys Thr Ser
        195                 200                 205

Gly Gly His Val Leu Asn Leu Gln Phe Asp Asn Ala Asn Leu Glu Ile
        210                 215                 220

Ser Pro Ile His Glu Phe Asp Val Gln Leu Pro His Thr Asp Asp Phe
225                 230                 235                 240

Ala His Ser Asp Leu Thr Gln Val Thr Thr Ser Gln Val His Gln Ala
                245                 250                 255

Glu Ser Glu Arg Lys
            260

<210> SEQ ID NO 4
<211> LENGTH: 783
<212> TYPE: DNA
<213> ORGANISM: artificial sequence
<220> FEATURE:
<223> OTHER INFORMATION: synthetic construct

<400> SEQUENCE: 4
gctacaacgg ctactgtacc agcaccacct gccaagcagg aatccaaacc tgcggttgcc      60
gctaatccgg caccaaaaaa tgtactgttt caatactcaa cgatcaatgc actcatgctt     120
ggacagtttg aagggacttg actttgaaag acctgaagct gcgaggcga tatgggcttt     180 ggtaccatca atgatctcga tggagagatg attcagatgg gtacaaaatt ctaccagatc     240
gacagcaccg aaaattatc ggagctgcca gaaagtgtga aaactccatt tgcggttact      300
acacatttcg agccgaaaga aaaaactaca ttaaccaatg tgcaagatta caatcaatta     360
acaaaaatgc ttgaggagaa atttgaaaac aagaacgtct tttatgccgt aaagctgacc     420
ggtactttta gatggtaaa ggctagaaca gttccaaaac aaaccagacc ttatccgcag      480
ctgactgaag taccaaaaa acaatccgag tttgaattta aaatgttaa gggaaccctg       540 attggcttct atacgccaaa ttatgcagca gccctgaatg ttcccggatt ccatctccac     600
ttcatcacag aggataaaac aagtggcgga cacgtattaa atctgcaatt tgacaacgcg     660
aatctggaaa tttctccgat ccatgagttt gatgttcaat tgccgcacac agatgatttt     720
gcccactctg atctgacaca agttactact agccaagtac accaagctga gtcagaaaga     780
aaa                                                                  783

<210> SEQ ID NO 5
<211> LENGTH: 290
<212> TYPE: PRT
<213> ORGANISM: artificial sequence
<220> FEATURE:
<223> OTHER INFORMATION: synthetic construct
```

<400> SEQUENCE: 5

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Thr Thr
            20                  25                  30

Ala Thr Val Pro Ala Pro Pro Ala Lys Gln Glu Ser Lys Pro Ala Val
        35                  40                  45

Ala Ala Asn Pro Ala Pro Lys Asn Val Leu Phe Gln Tyr Ser Thr Ile
    50                  55                  60

Asn Ala Leu Met Leu Gly Gln Phe Glu Gly Asp Leu Thr Leu Lys Asp
65                  70                  75                  80

Leu Lys Leu Arg Gly Asp Met Gly Leu Gly Thr Ile Asn Asp Leu Asp
                85                  90                  95

Gly Glu Met Ile Gln Met Gly Thr Lys Phe Tyr Gln Ile Asp Ser Thr
            100                 105                 110

Gly Lys Leu Ser Glu Leu Pro Glu Ser Val Lys Thr Pro Phe Ala Val
        115                 120                 125

Thr Thr His Phe Glu Pro Lys Glu Lys Thr Thr Leu Thr Asn Val Gln
    130                 135                 140

Asp Tyr Asn Gln Leu Thr Lys Met Leu Glu Glu Lys Phe Glu Asn Lys
145                 150                 155                 160

Asn Val Phe Tyr Ala Val Lys Leu Thr Gly Thr Phe Lys Met Val Lys
                165                 170                 175

Ala Arg Thr Val Pro Lys Gln Thr Arg Pro Tyr Pro Gln Leu Thr Glu
            180                 185                 190

Val Thr Lys Lys Gln Ser Glu Phe Glu Phe Lys Asn Val Lys Gly Thr
        195                 200                 205

Leu Ile Gly Phe Tyr Thr Pro Asn Tyr Ala Ala Ala Leu Asn Val Pro
    210                 215                 220

Gly Phe His Leu His Phe Ile Thr Glu Asp Lys Thr Ser Gly Gly His
225                 230                 235                 240

Val Leu Asn Leu Gln Phe Asp Asn Ala Asn Leu Glu Ile Ser Pro Ile
                245                 250                 255

His Glu Phe Asp Val Gln Leu Pro His Thr Asp Asp Phe Ala His Ser
            260                 265                 270

Asp Leu Thr Gln Val Thr Thr Ser Gln Val His Gln Ala Glu Ser Glu
        275                 280                 285

Arg Lys
    290

<210> SEQ ID NO 6
<211> LENGTH: 873
<212> TYPE: DNA
<213> ORGANISM: artificial sequence
<220> FEATURE:
<223> OTHER INFORMATION: synthetic construct

<400> SEQUENCE: 6
gtgagaagca aaaaattgtg gatcagcttg ttgtttgcgt taacgttaat ctttacgatg    60
gcgttcagca acatgagcgc gcaggctgct acaacggcta ctgtaccagc accacctgcc   120
aagcaggaat ccaaacctgc ggttgccgct aatccggcac caaaaaatgt actgtttcaa   180
tactcaacga tcaatgcact catgcttgga cagtttgaag gggacttgac tttgaaagac   240
ctgaagctgc gaggcgatat ggggcttggt gcaatcaatg atctcgatgg agagatgatt   300

-continued

```
cagatgggta caaaattcta ccagatcgac agcaccggaa aattatcgga gctgccagaa    360
agtgtgaaaa ctccatttgc ggttactaca catttcgagc cgaaagaaaa aactacatta    420
accaatgtgc aagattacaa tcaattaaca aaaatgcttg aggagaaatt tgaaaacaag    480
aacgtctttt atgccgtaaa gctgaccggt acttttaaga tggtaaaggc tagaacagtt    540
ccaaaacaaa ccagaccttta tccgcagctg actgaagtaa ccaaaaaaca atccgagttt    600
gaatttaaaa atgttaaggg aaccctgatt ggcttctata cgccaaatta tgcagcagcc    660
ctgaatgttc ccggattcca tctccacttc atcacagagg ataaaacaag tggcggacac    720
gtattaaatc tgcaatttga caacgcgaat ctggaaattt ctccgatcca tgagtttgat    780
gttcaattgc cgcacacaga tgattttgcc cactctgatc tgacacaagt tactactagc    840
caagtacacc aagctgagtc agaaagaaaa taa                                 873
```

<210> SEQ ID NO 7
<211> LENGTH: 290
<212> TYPE: PRT
<213> ORGANISM: artificial sequence
<220> FEATURE:
<223> OTHER INFORMATION: synthetic construct

<400> SEQUENCE: 7

```
Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Thr Thr
            20                  25                  30

Ala Thr Val Pro Ala Pro Pro Ala Lys Gln Glu Ser Lys Pro Ala Val
        35                  40                  45

Ala Ala Asn Pro Ala Pro Lys Asn Val Leu Phe Gln Tyr Ser Thr Ile
    50                  55                  60

Asn Ala Leu Met Leu Gly Gln Phe Glu Gly Asp Leu Thr Leu Lys Asp
65                  70                  75                  80

Leu Lys Leu Arg Gly Asp Met Gly Leu Gly Ala Ile Asn Asp Leu Asp
                85                  90                  95

Gly Glu Met Ile Gln Met Gly Thr Lys Phe Tyr Gln Ile Asp Ser Thr
            100                 105                 110

Gly Lys Leu Ser Glu Leu Pro Glu Ser Val Lys Thr Pro Phe Ala Val
        115                 120                 125

Thr Thr His Phe Glu Pro Lys Glu Lys Thr Thr Leu Thr Asn Val Gln
    130                 135                 140

Asp Tyr Asn Gln Leu Thr Lys Met Leu Glu Glu Lys Phe Glu Asn Lys
145                 150                 155                 160

Asn Val Phe Tyr Ala Val Lys Leu Thr Gly Thr Phe Lys Met Val Lys
                165                 170                 175

Ala Arg Thr Val Pro Lys Gln Thr Arg Pro Tyr Pro Gln Leu Thr Glu
            180                 185                 190

Val Thr Lys Lys Gln Ser Glu Phe Glu Phe Lys Asn Val Lys Gly Thr
        195                 200                 205

Leu Ile Gly Phe Tyr Thr Pro Asn Tyr Ala Ala Ala Leu Asn Val Pro
    210                 215                 220

Gly Phe His Leu His Phe Ile Thr Glu Asp Lys Thr Ser Gly Gly His
225                 230                 235                 240

Val Leu Asn Leu Gln Phe Asp Asn Ala Asn Leu Glu Ile Ser Pro Ile
                245                 250                 255

His Glu Phe Asp Val Gln Leu Pro His Thr Asp Asp Phe Ala His Ser
```

260                 265                 270
Asp Leu Thr Gln Val Thr Thr Ser Gln Val His Gln Ala Glu Ser Glu
            275                 280                 285
Arg Lys
    290

<210> SEQ ID NO 8
<211> LENGTH: 261
<212> TYPE: PRT
<213> ORGANISM: artificial sequence
<220> FEATURE:
<223> OTHER INFORMATION: synthetic construct

<400> SEQUENCE: 8

Ala Thr Thr Ala Thr Val Pro Ala Pro Pro Lys Gln Glu Ser Lys
1               5                   10                  15

Pro Ala Val Ala Ala Asn Pro Ala Pro Lys Asn Val Leu Phe Gln Tyr
                20                  25                  30

Ser Thr Ile Asn Ala Leu Met Leu Gly Gln Phe Glu Gly Asp Leu Thr
            35                  40                  45

Leu Lys Asp Leu Lys Leu Arg Gly Asp Met Gly Leu Gly Ala Ile Asn
    50                  55                  60

Asp Leu Asp Gly Glu Met Ile Gln Met Gly Thr Lys Phe Tyr Gln Ile
65                  70                  75                  80

Asp Ser Thr Gly Lys Leu Ser Glu Leu Pro Glu Ser Val Lys Thr Pro
                85                  90                  95

Phe Ala Val Thr Thr His Phe Glu Pro Lys Glu Lys Thr Thr Leu Thr
                100                 105                 110

Asn Val Gln Asp Tyr Asn Gln Leu Thr Lys Met Leu Glu Glu Lys Phe
            115                 120                 125

Glu Asn Lys Asn Val Phe Tyr Ala Val Lys Leu Thr Gly Thr Phe Lys
    130                 135                 140

Met Val Lys Ala Arg Thr Val Pro Lys Gln Thr Arg Pro Tyr Pro Gln
145                 150                 155                 160

Leu Thr Glu Val Thr Lys Lys Gln Ser Glu Phe Glu Phe Lys Asn Val
                165                 170                 175

Lys Gly Thr Leu Ile Gly Phe Tyr Thr Pro Asn Tyr Ala Ala Ala Leu
            180                 185                 190

Asn Val Pro Gly Phe His Leu His Phe Ile Thr Glu Asp Lys Thr Ser
    195                 200                 205

Gly Gly His Val Leu Asn Leu Gln Phe Asp Asn Ala Asn Leu Glu Ile
    210                 215                 220

Ser Pro Ile His Glu Phe Asp Val Gln Leu Pro His Thr Asp Asp Phe
225                 230                 235                 240

Ala His Ser Asp Leu Thr Gln Val Thr Thr Ser Gln Val His Gln Ala
                245                 250                 255

Glu Ser Glu Arg Lys
            260

ACETOLACTATE DECARBOXYLASE VARIANTS HAVING IMPROVED SPECIFIC ACTIVITY

CROSS-REFERENCE TO RELATED APPLICATIONS

This application is a U.S. national stage application under 35 U.S.C. § 371 of International Application No. PCT/EP2017/072915, filed on Sep. 12, 2017, which in turn claims priority to U.S. Provisional Application No. 62/395,592, filed on Sep. 16, 2016, the disclosures of each of which are incorporated herein by reference in their entireties.

BACKGROUND

Diacetyl is sometimes an unwanted by-product of fermentation processes of carbohydrate containing substances, e.g. wort or grape juice. Formation of diacetyl is most disadvantageous because of its strong and unpleasant smell and in case of beer even small amounts of diacetyl of about 0.10 to 0.15 mg/liter has a negative effect on the flavor and taste of the beer. During the maturation of beer, diacetyl is converted into acetoin by reductases in the yeast cells. Acetoin is with respect to taste and flavor acceptable in beer in much higher concentrations than diacetyl.

Acetolactate decarboxylase (ALDC) can also be used as an enzyme to prevent the formation of diacetyl. α-acetolactate can be converted into acetoin by adding an ALDC enzyme during fermentation. However, ALDC can be unstable at fermenting conditions, especially those of fermenting worts with low malt content.

Compositions and methods related to the use of acetolactate decarboxylases have been reported in International Patent Application No. PCT/US16/33028 and PCT/US16/33043.

However, there is an ongoing need to identify ALDC variants having improved properties, such as improved specific activity.

SUMMARY OF THE INVENTION

ALDC variants are provided having improved specific activity. The present improved variants can be incorporated into suitable methods, apparatuses, and kits.

Aspects and embodiments of the compositions and methods are set forth in the following separately numbered paragraphs.

1. A recombinant polypeptide having acetolactate decarboxylase (ALDC) activity is provide comprising
   (i) at least 80% amino acid identity to amino acid sequence of SEQ ID NO: 3 and wherein the polypeptide comprises at least one amino acid substitution at position 62 with reference to the position numbering of the sequence shown in SEQ ID NO: 3 or
   (ii) a functional fragment of (i) having a specific activity greater than or equal to the specific activity of (a).
2. The recombinant polypeptide of paragraph 1 having at least 90% amino acid identity to amino acid sequence of SEQ ID NO: 3
3. The recombinant polypeptide of paragraph 2 wherein the amino acid substitution is T62A.
4. The recombinant polypeptide of paragraph 3 having the amino acid sequence of SEQ ID NO: 8.
5. A composition comprising the recombinant polypeptide of paragraph 1, paragraph 2, paragraph 3 or paragraph 4 and zinc at concentration of about 1 μM to about 200 mM.
6. The composition of paragraph 5, wherein the zinc is present at a concentration of about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM.
7. The composition of paragraph 5 wherein the molar ratio of zinc to the recombinant polypeptide is
   (i) higher than 1; or
   (ii) 2:1 or higher; or
   (iii) 10:1 or higher; or
   (iv) 20:1 or higher; or
   (v) 30:1 or higher; or
   (vi) 60:1 or higher.
8. The composition of paragraph 5, wherein the recombinant polypeptide having acetolactate decarboxylase activity is treated with glutaraldehyde.
9. The composition of paragraph 8, wherein the recombinant polypeptide having acetolactate decarboxylase activity is treated with glutaraldehyde is at a concentration corresponding to about 0.1 grams to about 5 grams of glutaraldehyde per gram of recombinant polypeptide having acetolactate decarboxylase activity.
10. The composition according to any preceding paragraph, wherein the activity of said recombinant polypeptide having acetolactate decarboxylase activity is in the range of 950 to 3500 Units per mg of protein.
11. The composition of any preceding paragraph further comprising at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.
12. The composition of any preceding paragraph, wherein the recombinant polypeptide having acetolactate decarboxylase activity is derived from an acetolactate decarboxylase from *Bacillus brevis* or *Bacillus licheniformis*.
13. Use of the composition according to any preceding paragraph in beer and/or wine and/or cider and/or perry and/or sake fermentation.
14. A method for increasing the activity and/or stability of the recombinant polypeptide of paragraph 1 or paragraph 2 wherein said method comprises the step of adding zinc to a composition comprising the recombinant polypeptide so that said zinc is present in said composition at a concentration of about 1 μM to about 200 mM.
15. The method of paragraph 14, wherein said zinc is added at a concentration of 1 μM to about 5 mM.
16. A cultivation media for a recombinant host cell capable of producing the recombinant polypeptide of paragraph 1, paragraph 2, paragraph 3 or paragraph 4 comprising zinc at a concentration of about 1 μM to about 1 mM.
17. The cultivation media of paragraph 16, comprising zinc at concentration of about 60 μM to about 150 μM.
18. A beer, wine, cider, perry or sake fermentation media or maturation media comprising a composition comprising
   a) the recombinant polypeptide having acetolactate decarboxylase (ALDC) activity of paragraph 1, paragraph 2, paragraph 3 or paragraph 4, and;

b) zinc; wherein said composition comprises zinc at a concentration of about 1 µM to about 200 mM.

19. The beer, wine, cider, perry or sake fermentation media of maturation media of paragraph 18, wherein the activity of said recombinant polypeptide having acetolactate decarboxylase activity is in the range of 1000 to 3500 Units per mg of protein.

20. The beer, wine, cider, perry or sake fermentation media or maturation media of paragraph 19, further comprising at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

21. A method for beer, wine, cider, perry or sake production comprising adding a composition comprising the recombinant polypeptide having acetolactate decarboxylase (ALDC) activity of paragraph 1, paragraph 2, paragraph 3 or paragraph 4 and zinc to a media suitable for the beer, wine, cider, perry or sake production.

22. The method of paragraph 21 wherein
(i) zinc is present in the composition at a concentration of about 1 mM to about 5 mM; or
(ii) the molar ratio of zinc to the recombinant polypeptide having acetolactate decarboxylase activity in the composition is higher than 1; or 2:1 or higher; or 10:1 or higher; or 20:1 or higher; or 30:1 or higher; or 60:1 or higher.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

BRIEF DESCRIPTION OF THE BIOLOGICAL SEQUENCES

Figure 1:
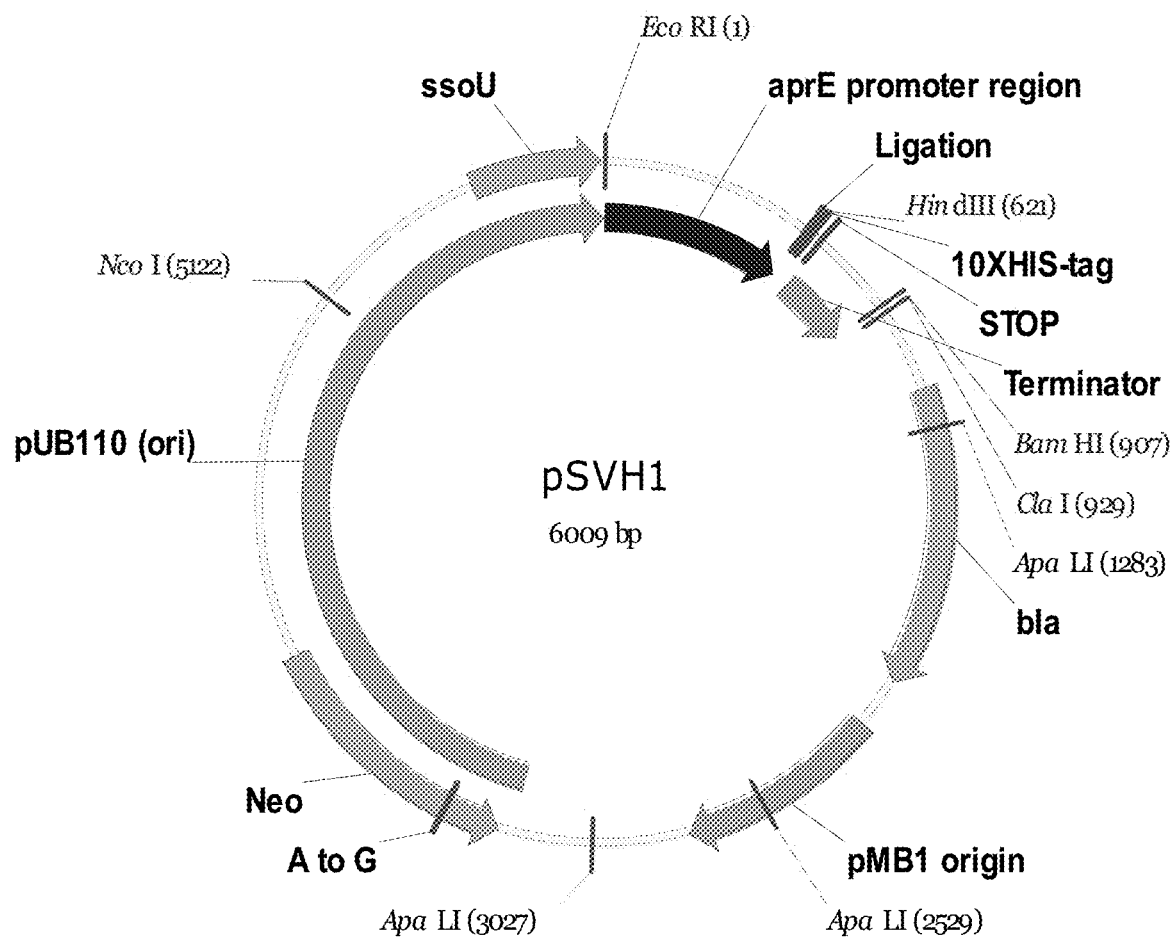
FIG. 1 shows a plasmid map for pSVH1.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO: 1 is polynucleotide sequence encoding the wild type aldB gene from *Brevibacillus brevis*.

SEQ ID NO: 2 is the polypeptide sequence of the wild type aldB precursor protein from *Brevibacillus brevis*.

SEQ ID NO: 3 is the polypeptide sequence of the wild type aldB mature protein from *Brevibacillus brevis*.

SEQ ID NO: 4 is the polynucleotide sequence of the aldB gene in plasmid pSVH1_Bbrev_aldB.

SEQ ID NO: 5 is the polypeptide sequence of the aldB precursor protein encoded by the aldB gene in plasmid pSVH1_Bbrev_aldB.

SEQ ID NO: 6 is the polynucleotide sequence encoding the aldB-T62A variant.

SEQ ID NO: 7 is the polypeptide sequence of the aldB-T62A variant precursor.

SEQ ID NO: 8 is the polypeptide sequence of the aldB-T62A mature protein.

DETAILED DESCRIPTION OF THE INVENTION

The present disclosure provides methods, compositions, apparatuses and kits comprising acetolactate decarboxylase variants having improved specific activity when compared to the parent enzyme from which they were derived.

In some embodiments, the present disclosure provides methods, apparatuses, compositions and kits for the use of metal ions to increase stability and/or activity, and, optionally, which further can be used to recover ALDC variant enzymes with improved properties.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

As used herein, the term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of".

As used herein, the term "about" modifying the quantity of an ingredient or reactant of the invention or employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

Unless otherwise indicated, any nucleic acid sequences are written left to right in 5' to 3' orientation; amino acid sequences are written left to right in amino to carboxy orientation, respectively.

It must be noted that as used herein and in the appended claims, the singular forms "a", "an", and "the" include plural referents unless the context clearly dictates otherwise. Thus, for example, reference to "a protease" includes a plurality of such enzymes and reference to "the feed" includes reference to one or more feeds and equivalents thereof known to those skilled in the art, and so forth.

As used herein, the term "enzyme catalyst" refers to a catalyst comprising an enzyme having ALDC activity and may be in the form of a whole microbial cell, permeabilized microbial cell(s), one or more cell components of a microbial cell extract, partially purified enzyme, or purified enzyme. The enzyme catalyst may also be chemically modified (e.g., by pegylation or by reaction with cross-linking reagents, such as glutaraldehdye). The enzyme catalyst may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid or as defined herein | Xaa | X |

As used herein, "substantially similar" refers to nucleic acid molecules wherein changes in one or more nucleotide bases results in the addition, substitution, or deletion of one or more amino acids, but does not affect the functional properties (i.e., ALDC activity) of the protein encoded by the DNA sequence. As used herein, "substantially similar" also refers to an enzyme having an amino acid sequence that is at least 40%, preferably at least 50%, more preferably at least 60%, more preferably at least 70%, even more preferably at least 80%, yet even more preferably at least 90%, and most preferably at least 95% identical to the sequences reported herein wherein the resulting enzyme retains the present functional properties (i.e., ALDC activity). "Substantially similar" may also refer to an enzyme having ALDC activity encoded by nucleic acid molecules that hybridizes under stringent conditions to the nucleic acid molecules reported herein. It is therefore understood that the invention encompasses more than the specific exemplary sequences.

For example, it is well known in the art that alterations in a gene which result in the production of a chemically equivalent amino acid at a given site, but do not affect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, and Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences are encompassed by the present invention. In one embodiment, substantially similar sequences are defined by their ability to hybridize, under stringent conditions (0.1× SSC, 0.1% SDS, 65° C. and washed with 2×SSC, 0.1% SDS followed by 0.1×SSC, 0.1% SDS, 65° C.) with the sequences exemplified herein.

As used herein, a nucleic acid molecule is "hybridizable" to another nucleic acid molecule, such as a cDNA, genomic DNA, or RNA, when a single strand of the first molecule can anneal to the other molecule under appropriate conditions of temperature and solution ionic strength. Hybridization and washing conditions are well known and exemplified in Sambrook, J. and Russell, D., T. *Molecular Cloning: A Laboratory Manual*, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar molecules, such as homologous sequences from distantly related organisms, to highly similar molecules, such as genes that duplicate functional enzymes from closely related organisms. Post-hybridization washes typically determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of conditions uses higher temperatures in which the washes are identical to those above except for the temperature of the final two 30 min washes in 0.2×SSC, 0.5% SDS was increased to 60° C. Another preferred set of stringent hybridization conditions is 0.1×SSC, 0.1% SDS, 65° C. and washed with 2×SSC, 0.1%

SDS followed by a final wash of 0.1×SSC, 0.1% SDS, 65° C. with the sequences exemplified herein.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (Sambrook and Russell, supra). For hybridizations with shorter nucleic acids, i.e., oligonucleotides, the position of mismatches becomes more important, and the length of the oligonucleotide determines its specificity (Sambrook and Russell, supra). In one aspect, the length for a hybridizable nucleic acid is at least about 10 nucleotides. Preferably, a minimum length for a hybridizable nucleic acid is at least about 15 nucleotides in length, more preferably at least about 20 nucleotides in length, even more preferably at least 30 nucleotides in length, even more preferably at least 300 nucleotides in length, and most preferably at least 800 nucleotides in length. Furthermore, the skilled artisan will recognize that the temperature and wash solution salt concentration may be adjusted as necessary according to factors such as length of the probe.

As used herein, the term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Sequence alignments and percent identity calculations may be performed using the Megalign program of the LASERGENE bioinformatics computing suite (DNASTAR Inc., Madison, Wis.), the AlignX program of Vector NTI v. 7.0 (Informax, Inc., Bethesda, Md.), or the EMBOSS Open Software Suite (EMBL-EBI; Rice et al., *Trends in Genetics* 16, (6):276-277 (2000)). Multiple alignment of the sequences can be performed using the Clustal method (i.e. CLUSTALW; for example, version 1.83) of alignment (Higgins and Sharp, *CABIOS,* 5:151-153 (1989); Higgins et al., *Nucleic Acids Res.* 22:4673-4680 (1994); and Chenna et al., *Nucleic Acids Res* 31 (13):3497-500 (2003)), available from the European Molecular Biology Laboratory via the European Bioinformatics Institute) with the default parameters. Suitable parameters for CLUSTALW protein alignments include GAP Existence penalty=15, GAP extension=0.2, matrix=Gonnet (e.g. Gonnet250), protein ENDGAP=−1, Protein GAPDIST=4, and KTUPLE=1. In one embodiment, a fast or slow alignment is used with the default settings where a slow alignment is preferred. Alternatively, the parameters using the CLUSTALW method (version 1.83) may be modified to also use KTUPLE=1, GAP PENALTY=10, GAP extension=1, matrix=BLOSUM (e.g. BLOSUM64), WINDOW=5, and TOP DIAGONALS SAVED=5.

In one aspect, suitable isolated nucleic acid molecules (isolated polynucleotides of the present invention) encode a polypeptide having an amino acid sequence that is at least about 80%, 85%, 90%, 95%, 97%, 98%, 99% or 100% identical to the amino acid sequences reported herein.

As used herein, "codon degeneracy" refers to the nature of the genetic code permitting variation of the nucleotide sequence without affecting the amino acid sequence of an encoded polypeptide. Accordingly, the present invention relates to any nucleic acid molecule that encodes all or a substantial portion of the amino acid sequences encoding the present polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

As used herein, the term "codon optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide for which the DNA codes.

As used herein, the term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., that the coding sequence is under the transcriptional control of the promoter. Coding sequences can be operably linked to regulatory sequences in sense or antisense orientation.

As used herein, the term "expression" refers to the transcription and stable accumulation of sense (mRNA) or antisense RNA derived from the nucleic acid molecule of the invention. Expression may also refer to translation of mRNA into a polypeptide.

As used herein, "transformation" refers to the transfer of a nucleic acid molecule into the genome of a host organism, resulting in genetically stable inheritance. In the present invention, the host cell's genome includes chromosomal and extrachromosomal (e.g. plasmid) genes. Host organisms containing the transformed nucleic acid molecules are referred to as "transgenic" or "recombinant" or "transformed" organisms.

As used herein, the term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), CLUSTALW (for example, version 1.83; Thompson et al., *Nucleic Acids Research,* 22(22):4673-4680 (1994), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified. As used herein "default values" will mean any set of values or parameters set by the software manufacturer that originally load with the software when first initialized.

All United States patents and patent application publications referred to herein are incorporated by reference in their entirety unless otherwise specified.

Acetolactate Decarboxylases (ALDC)

Acetolactate decarboxylases (ALDC) are enzymes that belongs to the family of carboxy lyases, which are responsible for cleaving carbon-carbon bonds. Acetolactate decarboxylases catalyze the conversion of 2-acetolactate (also known as 2-hydroxy-2-methyl-3-oxobutanoate) to 2-acetoin and releases $CO_2$. The terms "acetolactate decarboxylase(s)", "ALDC(s)", "ALDC enzyme(s)", "enzyme(s) having acetolactate decarboxylase activity", "polypeptide(s) having acetolactate decarboxylase activity" may be used interchangeably herein.

Acetolactate decarboxylase enzymes catalyze the enzymatic reaction belonging to the classification EC 4.1.1.5 (acetolactate decarboxylase activity) and gene ontology (GO) term ID of GO: 0047605. The GO term ID specifies that any protein characterized as having this associated GO term encodes an enzyme with catalytic acetolactate decarboxylase activity.

Various acetolactate decarboxylase genes (such as alsD or aldB), which encode acetolactate decarboxylase enzymes, are known in the art. The alsD gene, which encodes ALDC enzyme, may be derived or derivable from *Bacillus subtilis*. The aldB gene, which encodes ALDC enzyme, may be derived or derivable from *Bacillus brevis*. The alsD gene, which encodes ALDC enzyme, may be derived or derivable from *Bacillus licheniformis*. UNIPROT accession number Q65E52.1 is an example of an ALDC enzyme. UNIPROT accession number Q65E52.1 is an example of an ALDC enzyme derived or derivable from *Bacillus licheniformis*. Examples of acetolactate decarboxylase genes include, but are not limited to, those provided by sequences according to GENBANK® accession numbers YP_005006068.1, AEV96664.1, ACL05881.1, YP_002484831.1, YP_002433349.1, YP_002323676.1, YP_001959767.1, YP_001950964.1, YP_001814731.1, YP_001643659.1, YP_001530174.1, YP_001479659.1, YP_001317786.1, YP_001317390.1, YP_001176753.1, YP_663316.1, ACL46470.1, ACJ53298.1, ACD94444.1, ABW68097.1, ABV42531.1, ABP60702.1, ABR53499.1, ABR53103.1, ABY42031.1, ABG42262.1, ACE04286.1, ACB61714.1, ZP_03624564.1, ZP_03073518.1, EEF65194.1, EDX43464.1, YP_005422842.1, YP_005132076.1, YP_004758694.1, YP_004605085.1, YP_001247975.1, YP_001247593.1, YP_001270742.1, CCG51526.1, CCF06881.1, AEK35621.1, AE108921.1, ABQ82405.1, ABQ50399.1, ABQ50017.1, ZP_10276647.1, ZP_09451796.1, ZP_08659936.1, ZP_08575126.1, and UNIPROT Accession Nos. P23616.1 (Diderichsen et al., *J Bacteriol*. (1990) 172(8): 4315) and P23616.1.

As used herein, the terms "ALDC variant(s)", "variant ALDC", "variant ALDC enzymes", "ALDC variant enzymes", "polypeptide(s) having improved acetolactate decarboxylase activity", "variant polypeptide(s) having ALDC activity", "recombinant polypeptides having acetolactate decarboxylase activity", and "recombinant polypeptides having ALDC activity" will refer to the variant acetolactate decarboxylase enzymes as described herein having an improve property (e.g., increased specific activity) relative to the ALDC enzyme from which they were derived (i.e., the mature form of the *Brevibacillus brevis* ALDC having an amino acid sequence provided as SEQ ID NO: 3) when assayed under the same reaction conditions. In one aspect, the ALDC variants comprise at least one amino acid substitution at position 62 with reference to the position numbering of the sequence shown in SEQ ID NO: 3 (mature form). As used herein, the phrase "with reference to the position numbering" means amino acid residue position 62 using the residue numbering of SEQ ID ON: 3.

In one aspect, ALDC enzymes having improved specific activity are provided and, optionally, the yield of variant ALDC enzymes which can be recovered from microorganisms is improved.

As used herein, the term "improved specific activity" or "increased specific activity" refers to a variant acetolactate decarboxylase enzyme(s) having an increased acetolactate decarboxylase specific activity when compared to the ALDC activity of the enzyme from which the variant was derived (i.e, *Brevibacillus brevis* ALDC having an amino acid sequence provided as SEQ ID NO: 3) under the same reaction conditions. It is understood that the position number is relative to the mature form of the protein from which the variant was derived (SEQ ID NO: 3) and that the relative position numbering may shift when referring to the precursor protein (for example, SEQ ID NO: 2 for the *Brevibacillus brevis* ALDC).

In one embodiment, the fold increase in acetolactate decarboxylase specific activity for the present variants is at least 1.1, 1.2, 1.3, 1.4, 1.5, 1.6, 1.7, 1.8, 1.9, 2.0, 3.0, 4.0, 5.0, 6.0, 7.0, 8.0, 9.0, 10, 11, 12, or 13-fold when compared to the activity of the wild type sequence under substantially similar conditions.

The terms "host cell", "host microorganism", "strain" and "microorganism" may be used interchangeably herein.

It is to be understood that any suitable ALDC enzymes, i.e. ALDC produced from any microorganism which activity is dependent on metal ions, can be used. In some embodiments, the ALDC used in the present methods and compositions is an ALDC variant derived from an ALDC enzyme obtainable from *Bacillus brevis* or *Bacillus licheniformis*.

The ALDC activity of the enzyme composition is measured by the ALDC assays as described herein or any suitable assay known in the art. The standard assay is carried out at pH 6.0, and it can be performed at different pH values and temperatures for the additional characterization and specification of enzymes.

One unit of ALDC activity is defined as the amount of enzyme which produces 1 μmole acetoin per minute under the conditions of the assay (e.g., pH 6.0 (or as specified) and 30° C.

In some embodiments, the variant ALDC is a variant ALDC derivative. As used herein, the term "variant ALDC derivative" refers to the present ALDC variant(s) that have undergone chemical derivatization using a reactive compound, such as glutaraldehyde. In some embodiments, the variant ALDC derivative is characterized by the fact that variant ALDC in an aqueous medium is treated with or has been treated with glutaraldehyde. In some embodiments, the variant ALDC is treated with or has been treated with glutaraldehyde in a concentration corresponding to between 0.1 and 5 grams of glutaraldehyde per gram of (pure) variant ALDC protein, preferably corresponding to between 0.25 and 2 g of glutaraldehyde per g of (pure) variant ALDC protein.

In some embodiments, the variant ALDC enzyme comprises an amino acid sequence having at least 80%, 85%, 90%, 95%, 97%, 98%, 99% or 100% identity with SEQ ID NO: 3 (mature protein), wherein the polypeptide further comprises at least one amino acid substitution at position 62 with reference to the position numbering of SEQ ID NO: 3 (mature protein) or any functional fragments thereof so long as the amino acid substitution at position 62 is present. In one embodiment, the substitution is T62A. In a preferred embodiment, the variant ALDC comprises the amino acid sequence SEQ ID NO: 8 (mature protein).

In some embodiments, the enzyme has a temperature optimum in the range of 5-80° C., such as in the range of 5-40° C. or 15-80° C., such as in the range 20-80° C., such as in the range 5-15° C., 10-40° C., 10-50° C., 15-20° C., 45-65° C., 50-65° C., 55-65° C. or 60-80° C. In some embodiments, the enzyme has a temperature optimum of about 60° C.

In some embodiments, the enzyme has a total number of amino acids of less than 350, such as less than 340, such as less than 330, such as less than 320, such as less than 310, such as less than 300 amino acids, such as in the range of 200 to 350, such as in the range of 220 to 345 amino acids. In one embodiment, the variant enzyme (mature form) comprises about 261 amino acids.

In one embodiment, the amino acid sequence of the variant enzyme further comprises (in addition to the present substitution at position 62) at least one, two, three, four, five, six, seven, eight, nine or ten additional amino acid substitutions as compared to SEQ ID NO: 8, or any functional fragment thereof.

In some embodiments the compositions, media and methods comprise any one or more further enzyme(s). In some embodiments the one or more further enzyme(s) are selected from list consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, xylan acetyl esterase), protease, and combinations thereof.

In some embodiments the compositions, media and methods comprise an enzyme exhibiting acetolactate decarboxylase activity, wherein the activity of said enzyme is in the range of 950 to 3500 Units per mg of protein. In some embodiments the compositions, media and methods according to the invention comprise an enzyme exhibiting ALDC activity, wherein the activity of said ALDC enzyme is in the range of 1000 to 3500 Units per mg of protein. In some embodiments the compositions, media and methods according to the invention comprise an enzyme exhibiting ALDC activity, wherein the activity of said ALDC enzyme is in the range of 1500 to 3500 Units per mg of protein. In some embodiments, the compositions and method comprise an enzyme exhibiting ALDC activity is an enzyme comprising an amino acid sequence having at least 80% identity with SEQ ID NO: 3, wherein the polypeptide further comprises at least one amino acid substitution at position 62 with reference to the position numbering of SEQ ID NO: 3 or any functional fragments thereof. In a preferred embodiment, the present compositions and methods comprise a variant ALDC wherein the amino acid substitution is T62A. In a preferred embodiment, the present compositions and methods comprise a variant ALDC comprising the amino acid sequence SEQ ID NO: 8 (mature protein).

Protein Engineering

It is contemplated that the present nucleotides may be used to produce gene products having further enhanced or altered activity. Various methods are known for mutating a native gene sequence to produce a gene product with altered or enhanced activity including, but not limited to 1) random mutagenesis, 2) domain swapping (using zinc finger domains or restriction enzymes, 3) error-prone PCR (Melnikov et al., *Nucleic Acids Research* 27(4):1056-1062 (1999)); 4) site directed mutagenesis (Coombs et al., *Proteins* (1998), pp 259-311, 1 plate. Angeletti, Ruth Hogue, Ed., Academic: San Diego, Calif.); and 5) "gene shuffling" (U.S. Pat. Nos. 5,605,793; 5,811,238; 5,830,721; and 5,837,458, incorporated herein by reference).

The polymerase chain reaction (PCR) can be used to amplify a DNA fragment with the concomitant creation of numerous mutations by mis-incorporation of nucleotides. This can be achieved by modifying the PCR conditions such as altering the ratios of dNTPs or adding various amounts of manganese chloride in the reaction (Fromant et al., *Anal Biochem*, 224(1):347-53 (1995); Lin-Goerke et al., *Biotechniques*, 23(3):409-12 (1997)). The pool of mutated DNA fragments can then be cloned to yield a library of mutated plasmids that can then be screened following expression in a host such as *E. coli*.

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions having similarity and/or difference to the gene of interest. This pool of fragments will then be denatured and reannealed to create a mutated gene. The mutated gene is then screened for altered activity.

The instant sequences of the present invention may be mutated and screened for altered or enhanced activity by this method. The sequences should be double-stranded and can be of various lengths ranging from 50 bp to 10 kB. The sequences may be randomly digested into fragments ranging from about 10 bp to 1000 bp, using restriction endonuclease well known in the art (Sambrook, J. and Russell, supra). In addition to the instant microbial sequences, populations of fragments that are hybridizable to all or portions of the sequence may be added. Similarly, a population of fragments, which are not hybridizable to the instant sequence, may also be added. The additional fragment populations are typically added in about a 10- to 20-fold excess by weight as compared to the total nucleic acid. Generally, if this process is followed, the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double-stranded nucleic acid. Preferably the temperature is from about 80° C. to 100° C. The nucleic acid fragments may be reannealed by cooling. Preferably the temperature is from about 20° C. to 75° C. Renaturation may be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTPs (i.e., dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from about 2 to 50 times, more preferably the sequence is repeated from 10 to 40 times. The resulting nucleic acid is a larger double-stranded polynucleotide ranging from about 50 bp to about 100 kB and may be screened for expression and altered activity by standard cloning and expression protocols (Sambrook, J. and Russell, supra).

Furthermore, a hybrid protein can be assembled by fusion of functional domains using gene shuffling (e.g., Nixon et al., *PNAS*, 94:1069-1073 (1997)). The functional domain of the instant gene may be combined with the functional domain of other genes to create novel enzymes with desired catalytic function. A hybrid enzyme may be constructed using PCR overlap extension methods and cloned into various expression vectors using the techniques well known to those skilled in art.

Metal Ions

In one aspect, methods and compositions comprising variant ALDC enzymes are provided having a better specific activity. In another aspect, methods and compositions are provided comprising variant ALDC enzymes which can be recovered from microorganisms in improved yields.

Treatment of variant ALDC compositions with certain metal ions at certain concentrations provides ALDC enzymes having a better stability and/or activity, and, optionally, the yield of ALDC activity which can be recovered from microorganisms is improved.

In some embodiments, the atomic radius for the metal ion is about 140 pm to about 255 pm. In some embodiments, the atomic radius for the metal ion is about 140 pm to about 165 pm. In some embodiments, the atomic radius for the metal ion is about 140 pm to about 150 pm. In some embodiments, the atomic radius for the metal ion is about 142 pm to about 146 pm.

In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. The term "zinc" as used herein may be interchangeable with the term "$Zn^{2+}$". The term "metal" as used herein may be interchangeable with the term "metal ion". The term "metal" as used herein may refer to compounds which comprise the metal selected from the group consisting of zinc, magnesium, manganese, cobalt, copper, barium, calcium and iron; compounds which comprise these metals are a source of the respective ions. The term "zinc" as used herein refers to compounds which comprise zinc, such compounds are a source of $Zn^{2+}$ ions. Zinc sulfate ($ZnSO_4$) is example of zinc as referred to herein and is an example of a source of $Zn^{2+}$ ions. Magnesium sulfate ($MgSO_4$) is an example of magnesium as referred to herein and is an example of a source of $Mg^{2+}$ ions. Manganese(II) sulfate ($MnSO_4$) is an example of manganese as referred to herein and is an example of a source of $Mn^{2+}$ ions. Cobalt(II)chloride ($CoCl_2$) is an example of cobalt as referred to herein and is an example of a source of $Co^{2+}$ ions. Copper(II) sulphate ($CuSO_4$) is an example of copper as referred to herein and is an example of a source of $Cu^{2+}$ ions. Barium sulfate ($BaSO_4$) is an example of barium as referred to herein and is an example of a source of $Ba^{2+}$ ions. Calcium sulfate ($CaSO_4$) is an example of calcium as referred to herein and is example of a source of $Ca^{2+}$ ions. Iron(II) sulfate ($FeSO_4$) is an example of iron as referred to herein and is example of a source of $Fe^{2+}$ ions.

Metal ions such as $Zn^{2+}$, $Mn^{2+}$, $Co^{2+}$, $Cu^{2+}$, and $Fe^{2+}$ increase the stability of the variant ALDC enzyme(s) in different formulations (see Examples), and also improve the recovery yields from microorganisms when the metal ions are used during the production of the enzyme in the cultivation media. Thus, in some embodiments, methods and compositions are provided that increase the recovery yields, stability and/or activity of variant ALDC enzymes that can be then used, e.g., to produce fermented products such as in brewing.

In some embodiments, the variant ALDC has an specific activity of at least about 900 units per mg of protein (U/mg), at least about 1000 U/mg, at least about 1500 U/mg, at least about 2000 U/mg, at least about 3000 U/mg at least about 5000 U/mg, at least about 6000 U/mg, at least about 7000 U/mg, at least about 8000 U/mg, at least about 8500 U/mg, at least about 9000 U/mg, at least about 9500 U/mg, or at least about 10000 U/mg as measured by the assays described herein or any suitable assay known in the art. In some embodiments, the variant ALDC has an ALDC activity in the range of about 950 to 3500 units per mg of protein (U/mg), about 1000 to 3500 U/mg, or about 1500 to 3500 U/mg as measured by the assays described herein or any suitable assay known in the art. In some embodiments, the present compositions and methods comprise a variant ALDC with ALDC activity of at least about 900 units per gram of product, at least about 1000 U/g, at least about 1500 U/g, at least about 2000 U/g, at least about 3000 U/g at least about 5000 U/g, such as at least about 6000 U/g, such as at least about 7000 U/g, such as at least about 8000 U/g, such as at least about 8500 U/g, such as at least about 9000 U/g, such as at least about 9500 U/g, such as at least about 10000 U/g as measured by in the assays described herein or any suitable assay known in the art. In some embodiments, a different ALDC activity is used, e.g., depending on the acetolactate content and conditions requirements, e.g. for brewing. In some embodiments, the present compositions and methods comprise a variant ALDC with ALDC activity of at least about 8000 U/g.

In some embodiments, the present compositions and methods comprise a variant ALDC and a metal ion, where the metal ion is present at a concentration of about 0.1 µM to about 200 mM, such as about 1 µM to about 200 mM, or about 1 µM to about 500 µM, or about 1 µM to about 300 µM, or about 6 µM to about 300 µM, or about 10 µM to about 100 µM, or about 15 µM to about 50 µM, or about 1 µM to about 150 mM, or about 10 µM to about 150 mM, or about 20 µM to about 120 mM, or about 25 µM to about 100 mM, or about 25 µM to about 50 mM, or about 25 µM to about 20 mM, or about 25 µM to about 50 mM, or about 100 µM to about 20 mM, or about 250 µM to about 20 mM, or about 1 mM to about 20 mM, or about 1 µM to about 5 mM. In some embodiments, the present compositions and methods comprise a variant ALDC and a metal ion, where the metal ion is present at a concentration of about 1 µM to about 300 µM, such as about 6 µM to about 300 µM, or about 6 µM to about 50 µM, or about 6 µM to about 25 µM. In some embodiments, the compositions and methods comprise a variant ALDC and a metal ion, where the metal ion is present at a concentration of about 60 µM to about 150 µM, or about 60 µM to about 150 µM. In some embodiments, the present compositions and methods comprise a variant ALDC and a metal ion, where the metal ion is present at a concentration of about 100 µM to about 200 mM. In some embodiments, the present compositions and methods comprise a variant ALDC and a metal ion, where the metal ion is present at a concentration of about 100 µM to about 20 mM. In some embodiments, the present compositions and methods comprise a variant ALDC and a metal ion, where the metal ion is present at a concentration of about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$.

In some embodiments, the present compositions and methods comprise a variant ALDC and zinc where the zinc is present at a concentration of about 1 µM to about 200 mM, such as about 1 µM to about 500 µM, or about 1 µM to about 300 µM, or about 6 µM to about 300 µM, or about 10 µM to about 100 µM, or about 15 µM to about 50 µM, or about 10 µM to about 150 mM, or about 20 µM to about 120 mM, or about 25 µM to about 100 mM, or about 25 µM to about 50 mM, or about 25 µM to about 20 mM, or about 25 µM to about 50 µM, or about 100 µM to about 20 mM, or about 250 µM to about 20 mM, or about 500 µM to about 20 mM, or about 1 mM to about 20 mM, or about 1 mM to about 10 mM, or about 1 mM to about 5 mM, or about 5 mM to about 20 mM, or about 5 mM to about 10 mM. In some embodiments, the present compositions and methods comprise a variant ALDC and zinc, where the zinc is present at a concentration of about 1 µM to about 300 µM, such about 6 µM to about 300 µM, or about 6 µM to about 25 µM. In some embodiments, the compositions and methods comprise a variant ALDC and zinc, where the zinc is present at a concentration of about 25 µM to about 150 µM or about 60 µM to about 150 µM. In some embodiments, the compositions and methods comprise a variant ALDC and zinc, where the zinc is present at a concentration of about 100 µM to about 20 mM. In some embodiments, the compositions and methods comprise a variant ALDC and zinc, where the zinc is present at a concentration of about 100 µM to about 10 mM. In some embodiments, the compositions and methods comprise a variant ALDC and zinc, where the zinc is present at a concentration of about 1 mM to about 5 mM.

In some embodiments, the compositions and methods comprise a variant ALDC and zinc where the zinc is present at a concentration of about 1 mM to about 3 mM, or about 0.75 mM to about 4 mM, or about 0.5 mM to about 5 mM, or about 0.25 mM to about 7.5 mM, or about 0.1 mM to about 10 mM. In some embodiments, the activity of said variant ALDC is in the range of 950 to 3500 Units per mg of protein, or 1000 to 3500 Units per mg of protein, or 1500 to 3500 Units per mg of protein.

In some embodiments, the present compositions and/or methods comprise a variant ALDC and zinc, where the molar ratio of zinc to enzyme is higher than 1 such as 2:1, or 3:1, or 5:1, or 10:1, or 20:1 or 30:1 or 50:1, or 60:1, or 100:1, or 150:1, or 200:1, or 250:1, or 500:1. In some embodiments, the compositions comprise a variant ALDC and zinc, where the molar ratio of zinc to enzyme is 2:1 or higher. In some embodiments, the compositions and/or methods comprise a variant ALDC and zinc, where the molar ratio of zinc to enzyme is 5:1 or higher. In some embodiments, the compositions and/or methods comprise a variant ALDC and zinc, where the molar ratio of zinc to enzyme is 10:1 or higher. In some embodiments, the compositions and/or methods comprise a variant ALDC and zinc, where the molar ratio of zinc to enzyme is 20:1 or higher. In some embodiments, the compositions and/or methods comprise a variant ALDC and zinc, where the molar ratio of zinc to enzyme is 30:1 or higher. In some embodiments, the compositions and/or methods comprise a variant ALDC and zinc, where the molar ratio of zinc to enzyme is 60:1 or higher. The molar concentration of, for example, $Zn^{2+}$, $Mn^{2+}$, $Co^{2+}$ or other metal ions in solution may be determined by inductively coupled plasma optical emission spectrometry (ICP-OES) or similar techniques. The molar concentration of the variant ALDC may be determined using Criterion SDS-PAGE system (such as described in the examples) and the amino acid sequence.

In some embodiments, the variant ALDC is a variant ALDC derivative. In some embodiments, the variant ALDC derivative is a variant ALDC enzyme treated with glutaraldehyde. In some embodiments, the variant ALDC enzyme is treated with glutaraldehyde at a concentration corresponding to about 0.1 to about 5 g of glutaraldehyde per g of (preferably pure) variant ALDC.

In some embodiments, the variant ALDC enzyme compositions described herein are used during fermentation and/or maturation of a beverage preparation process, e.g., beer and wine, to reduce diacetyl levels. The terms "variant ALDC enzyme composition", "composition comprising a variant ALDC" and "composition comprising variant ALDC" as used herein refer to compositions comprising the variant ALDC (enzyme) (or combination of variant ALDC (enzymes)). The composition may be in the form of a solution. As used herein, the terms "variant ALDC enzyme composition" and "compositions comprising ALDC variants" are mutually exclusive with media (such as cultivation media, fermentation media or maturation media) which comprise microorganisms expressing the ALDC variant and/or capable of expressing the ALDC variant when cultured under conditions permitting expression of the enzyme. Examples of variant ALDC compositions and compositions comprising ALDC variant(s) include compositions comprising the ALDC variant in a purified form. The ALDC variant may be purified from a media comprising microorganisms capable of expressing the ALDC variant wherein said media has been cultured under conditions permitting expression of the ALDC variant. The term "purified" means that the ALDC variant is present at a high level. Preferably, the ALDC variant is the predominant component present in the composition. Preferably, ALDC is present at a level of at least about 90%, or at least about 95% or at least about 98%, said level being determined on a dry weight/dry weight basis with respect to the total composition under consideration. In some embodiments, the ALDC variant (enzyme) composition further comprises a metal ion such as zinc.

As used herein, the terms "beverage" and "beverage(s) product" include such foam forming fermented beverages as beer brewed with 100% malt, beer brewed under different types of regulations, ale, dry beer, near beer, light beer, low alcohol beer, low calorie beer, porter, bock beer, stout, malt liquor, non-alcoholic beer, non-alcoholic malt liquor and the like. The term "beverages" or "beverages product" also includes non-foaming beer and alternative malt beverages such as fruit flavored malt beverages, for example, citrus flavored, such as lemon-, orange-, lime-, or berry-flavored malt beverages, liquor flavored malt beverages, for example, vodka-, rum-, or tequila-flavored malt liquor, or coffee flavored malt beverages, such as caffeine-flavored malt liquor, and the like. The term "beverages" or "beverages product" also includes beer made with alternative materials other than malted barley, such as rye, corn, oats, rice, millet, triticale, cassava, sorghum, barley, wheat and a combination thereof. The term "beverages" or "beverages product" also includes other fermented products such as wine or ciders or perry or sake.

Beer is traditionally referred to as an alcoholic beverage derived from malt, such as malt derived from barley grain, and optionally adjunct, such as starch containing plant material (for example, cereal grains) and optionally flavored, for example, with hops. The term "beer" includes any fermented wort, produced by fermentation/brewing of a starch-containing plant material, thus in particular also beer produced exclusively from adjunct, or any combination of malt and adjunct. Beer can be made from a variety of starch-containing plant material by essentially the same process, where the starch consists mainly of glucose homopolymers in which the glucose residues are linked by alpha-1,4- or alpha-1,6-bonds, with the former predominating. Beer can be made from alternative materials such as rye, corn, oats, rice, millet, triticale, cassava, sorghum, wheat, barley and a combination thereof.

In some embodiments, a fermentation media (e.g. beer, wine, cider, perry or sake fermentation) is provided comprising an ALDC variant and metal ion at a concentration of about 0.1 µM to about 200 mM, or about 1 µM to about 200 mM, such as about 1 µM to about 500 µM, or about 0.1 µM to about 300 µM, or about 1 µM to about 300 µM, or about 6 µM to about 300 µM, or about 1 µM to about 100 µM, or about 1 µM to about 50 µM, or about 6 µM to about or about 6 µM to about 25 µM. In some embodiments, the invention provides a composition comprising an ALDC variant and metal ion at a concentration of about 0.1 µM to about 100 mM, such as about 0.1 µM to about 10 µM, or 1 µM to about 100 mM, or 1 µM to about 10 µM, or 6 µM to about 10 µM, or about 10 µM to about 200 µM, or about 50 µM to about 1 mM, or about 100 µM to about 10 mM, or about 100 µM to about 50 mM, or about 100 µM to about 100 mM, or about 100 µM to about 200 mM, or about 250 µM to about 120 mM, or about 500 µM to about 100 mM, or about 1 mM to about 50 mM, or about 1 mM to about 20 mM, or about 1 mM to about 5 mM. In some embodiments, a fermentation media (e.g. beer, wine, cider, perry or sake fermentation) is provided comprising an ALDC variant and metal ion at a concentration of about 0.1 µM to about 200 mM or about 1 µM to about 200 mM, such as about 1 µM to about 500 µM, or about 1 µM to about 300 µM, or about 6 µM to about 300 µM, or about 1 µM to about 100 µM, or about 1 µM to about 50 µM, or about 6 µM to about 50 µM, or about 6 µM to about 25 µM. In some embodiments, a fermentation media is provided comprising an ALDC variant (enzyme) and metal ion at a concentration of about 1 µM to about 300 µM, or about 6 µM to about 300 µM, or about 1 µM to about 100 µM, or about 1 µM to about 50 µM, or about 6 µM to about 50 µM or about 6 µM to about 25 µM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC variant is in the range of 950 to 3500 Units per mg of protein, or 1000 to 3500 Units per mg of protein, or 1500 to 3500 Units per mg of protein. In some embodiments, the fermentation media (e.g. beer, wine, cider, perry or sake fermentation) further comprises at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

In some embodiments, a maturation media (e.g. beer, wine, cider, perry or sake fermentation) is provided comprising an ALDC variant and metal ion at a concentration of about 0.1 µM to about 200 mM, 1 µM to about 200 mM, such as about 1 µM to about 500 µM, about 0.1 µM to about 300 µM, about 1 µM to about 300 µM, about 6 µM to about 300 µM, about 1 µM to about 100 µM, about 1 µM to about 50 µM, about 6 µM to about 50 µM or about 6 µM to about 25 µM. In some embodiments, a composition is provided comprising an ALDC variant and metal ion at a concentration of about 0.1 µM to about 100 mM, 1 µM to about 100 mM, such as about 0.1 µM to about 10 µM, 1 µM to about 10 µM, 6 µM to about 10 µM, about 10 µM to about 200 µM, about 50 µM to about 1 mM, about 100 µM to about 10 mM, about 100 µM to about 50 mM, about 100 µM to about 100 mM, about 100 µM to about 200 mM, about 250 µM to about 120 mM, about 500 µM to about 100 mM, about 1 mM to about 50 mM, about 1 mM to about 20 mM or about 1 mM to about 5 mM. In some embodiments, a maturation media (e.g. beer, wine, cider, perry or sake fermentation) is provided comprising an ALDC variant and metal ion at a concentration of about 1 µM to about 500 µM, about 1 µM to about 300 µM, about 6 µM to about 300 µM, about 1 µM to about 100 µM, about 1 µM to about 50 µM, about 6 µM to about 50 µM or about 6 µM to about 25 µM. In some embodiments, a maturation media (e.g. beer, wine, cider, perry or sake fermentation) is provided comprising an ALDC variant and metal ion at a concentration of about 1 µM to about 300 µM, about 6 µM to about 300 µM, about 1 µM to about 100 µM, about 1 µM to about 50 µM, about 6 µM to about 50 µM or about 6 µM to about 25 µM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC variant is in the range of 950 to 3500 Units per mg of protein, or 1000 to 3500 Units per mg of protein, or 1500 to 3500 Units per mg of protein. In some embodiments, the maturation media (e.g. beer and/or wine maturation) further comprises at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endo-glucanase and related beta-glucan hydrolytic accessory enzymes, xylanase, xylanase accessory enzymes (for example, arabinofuranosidase, ferulic acid esterase, and xylan acetyl esterase) and protease.

In some embodiments, metal ions such as $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof are added to the cultivation and/or fermentation media during and/or after ALDC variant production to increase the recovered yields from microorganisms.

The term "cultivation media", as used herein, refers to a media which supports the growth of microorganisms, such as an ALDC variant-producing recombinant host cell. Examples of a cultivation media include: media based on MOPs buffer with, for instance, urea as the major nitrogen source and maltrin as the main carbon source; and TSB broth. In some embodiments, a cultivation media is provided for an ALDC variant-producing host cell comprising a metal ion at a concentration of about 1 μM to about 1 mM. In some embodiments, a cultivation media is provided for an ALDC variant-producing host cell comprising a metal ion at a concentration of about 25 μM to about 150 μM. In some embodiments, the invention provides a cultivation media for an ALDC producing host cell comprising a metal ion at a concentration of about 25 μM to about 50 μM. In some embodiments, the invention provides a cultivation media for an ALDC producing host cell comprising a metal ion at a concentration of about 30 μM to about 40 μM. In some embodiments, the invention provides a cultivation media for an ALDC producing host cell comprising a metal ion at a concentration of about 40 μM to about 150 μM. In some embodiments, the invention provides a cultivation media for an ALDC producing host cell comprising a metal ion at a concentration of about 60 μM to about 150 μM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said ALDC enzyme is in the range of 950 to 3500 Units per mg of protein, or 1000 to 35000 Units per mg of protein, or 1500 to 3500 Units per mg of protein.

Materials may be added to an enzyme-containing composition to improve the properties of the composition. Non-limiting examples of such additives include: salts (e.g., alkali salts, earth metal salts, additional chloride salts, sulfate salts, nitrate salts, carbonate salts, where exemplary counter ions are calcium, potassium, and sodium), inorganic minerals or clays (e.g., zeolites, kaolin, bentonite, talcs and/or silicates), carbohydrates (e.g., sucrose and/or starch), coloring pigments (e.g., titanium dioxide), biocides (e.g., Rodalon®, Proxel®), dispersants, anti-foaming agents, reducing agents, acid agents, alkaline agents, enzyme stabilizers (e.g. polyol such as glycerol, propylene glycol, sorbitol, inorganic salts, sugars, sugar or a sugar alcohol, lactic acid, boric acid, or a boric acid derivative and combinations thereof), enzyme inhibitors, preservative (e.g. methyl paraben, propyl paraben, benzoate, sorbate or other food approved preservatives) and combinations thereof. Excipients which may be used in the composition, or the preparation thereof, include maltose, maltose syrup, sucrose, glucose (including glucose syrup or dried glucose syrup), pre-cooked starch, gelatinised starch, L-lactic, ascorbyl palmitate, tocopherols, lecithins, citric acid, citrates, phosphoric, phosphates, sodium alginate, carrageenan, locust bean gum, guar gum, xanthan gum, pectins, sodium carboxymethylcellulose, mono- and diglycerides, citric acid esters of mono- and diglycerides, sucrose esters, carbon dioxide, argon, helium, nitrogen, nitrous oxide, oxygen, hydrogen, and starch sodium octenylsuccinate.

Methods

In some aspects the invention provides methods to improve stability and/or activity of variant ALDC enzymes. In some aspects the invention provides methods to improve ALDC variant recovery from microorganisms.

In some embodiments, the invention provides methods for increasing the activity and/or stability of a variant ALDC in a composition comprising the ALDC variant wherein said method comprises the step of adding a metal ion to the composition so that said metal ion is present in said composition at a concentration of about 1 μM to about 200 mM, such as about 1 μM to about 500 μM, or about 1 μM to about 300 μM, or about 6 μM to about 300 μM, or about 1 μM to about 100 μM, or about 1 μM to about 50 μM, or about 10 μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM, or about 5 mM to about 20 mM, or about 5 mM to about 10 mM. In some embodiments, the invention provides methods for increasing the activity and/or stability of a variant ALDC in a cultivation media comprising the ALDC variant-producing host cell wherein said method comprises the step of adding a metal ion to the media so that said metal ion is present in said media at a concentration of about 1 μM to about 1 mM, such as about 1 μM to about 300 μM, about 6 μM to about 300 μM, about 25 μM to about 150 μM, or about 60 μM to about 150 μM. In some embodiments, the invention provides methods for increasing the activity and/or stability of a variant ALDC in a fermentation and/or maturation media comprising a variant ALDC wherein said method comprises the step of adding a metal ion to the media so that said metal ion is present in said media at a concentration of about 1 μM to about 300 μM, such as about 6 μM to about 300 μM, about 1 μM to about 100 μM, about 1 μM to about 50 μM, about 1 μM to about 25 μM, or about 6 μM to about 25 μM. In some embodiments, the invention provides methods for increasing the activity and/or stability of an ALDC variant comprising adding a metal ion at a concentration of about 25 μM to about 150 μM in a media. In some embodiments, the invention provides methods for increasing the activity and/or stability of an ALDC variant comprising adding a metal ion at a concentration of about 100 μM to about 20 mM. In some embodiments, the invention provides methods for increasing the activity and/or stability of an ALDC variant comprising adding a metal ion at a concentration of about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$.

In some embodiments, the invention provides methods for increasing the activity and/or stability of an ALDC variant (enzyme) in a composition comprising the ALDC variant wherein said method comprises the step of adding a zinc to the composition so that said zinc is present in said composition at a concentration of about 1 μM to about 200 mM, such as about 1 μM to about 500 μM, or about 1 μM to about 300 μM, or about 6 μM to about 300 μM, or about 1 μM to about 100 μM, or about 1 μM to about 50 μM, or about 10

μM to about 150 mM, or about 20 μM to about 120 mM, or about 25 μM to about 100 mM, or about 25 μM to about 50 mM, or about 25 μM to about 20 mM, or about 25 μM to about 50 μM, or about 100 μM to about 20 mM, or about 250 μM to about 20 mM, or about 500 μM to about 20 mM, or about 1 mM to about 20 mM, or about 1 mM to about 10 mM, or about 1 mM to about 5 mM, or about 5 mM to about 20 mM, or about 5 mM to about 10 mM. In some embodiments, the invention provides methods for increasing the activity and/or stability of an ALDC variant in a cultivation media comprising an ALDC variant-producing (recombinant) host cell wherein said method comprises the step of adding a zinc at a concentration of about 1 μM to about 1 mM, such as about 1 μM to about 300 μM, about 6 μM to about 300 μM, about 25 μM to about 150 μM, or about 60 μM to about 150 μM. In some embodiments, the invention provides methods for increasing the activity and/or stability of an ALDC variant in a fermentation and/or maturation media comprising the ALDC variant wherein said method comprises the step of adding a zinc to the media so that said zinc is present in said media at a concentration of about 1 μM to about 300 μM, such as about 6 μM to about 300 μM, about 1 μM to about 100 μM, about 1 μM to about 50 μM, about 1 μM to about 25 μM, or about 6 μM to about 25 μM. In some embodiments, methods for increasing the activity and/or stability of an ALDC variant comprise adding a zinc to a media so that the zinc is at a concentration of about 25 μM to about 150 μM in the media. In some embodiments, methods for increasing the activity and/or stability of an ALDC variant comprise adding a zinc at a concentration of about 100 μM to about 20 mM. In some embodiments, methods for increasing the activity and/or stability of an ALDC variant comprise adding a zinc at a concentration of about 1 mM to about 5 mM. In some embodiments, methods for increasing the activity and/or stability of an ALDC variant comprise adding zinc at a molar ratio of zinc to variant ALDC that is higher than 1 such as 2:1, or 3:1, or 5:1, or 10:1, or 20:1 or 30:1, or 50:1, or 60:1, or 100:1, or 150:1, or 200:1 or 250:1 in said composition. In some embodiments, methods for increasing the activity and/or stability of an ALDC variant comprise adding zinc at a molar ratio of zinc to ALDC variant of 5:1 or higher in said composition. In some embodiments, methods for increasing the activity and/or stability of an ALDC variant comprise adding zinc at a molar ratio of zinc to ALDC variant of 10:1 or higher in said composition. In some embodiments, methods for increasing the activity and/or stability of an ALDC variant comprise adding zinc at a molar ratio of zinc to ALDC variant of 20:1 or higher in said composition. In some embodiments, methods for increasing the activity and/or stability of an ALDC variant comprise adding zinc at a molar ratio of zinc to ALDC variant of 30:1 or higher in said composition.

In some embodiments, the metal ion is added (e.g. as a supplement) to a cultivation media during the production of said ALDC variant enzyme by an ALDC variant-producing host cell. In some embodiments, the metal ion is added at a concentration of about 0.1 μM to about 1 mM, such as about 25 μM to about 150 μM, or about 40 μM to about 150 μM, or about 60 μM to about 150 μM, or about 25 μM to about 50 μM, or 30 μM to about 40 μM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments zinc is added (e.g. as a supplement) to a cultivation media during the production of said ALDC variant by an ALDC variant-producing host cell at a concentration of 1 μM to about 1 mM, such as 25 μM to about 150 μM, or about 40 μM to about 150 μM, or 60 μM to about 150 μM.

In some embodiments, the host cell is a *Bacillus* host cell. In some embodiments, *Bacillus* host cell is *Bacillus subtilis*.

In some embodiments, the metal ion is added in the fermentation media during production of a fermented beverage. In some embodiments, the metal ion is added in the fermentation media during beer, wine, cider, perry or sake fermentation. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments, zinc is added in a fermentation media during beer, wine, cider, perry or sake fermentation. In some embodiments, zinc is added at a concentration of about 1 μM to about 1 mM, such as about 1 μM to about 300 μM, or about 6 μM to about 300 μM, or about 1 μM to about 100 μM, or 25 μM to about 50 μM, or 30 μM to about 40 μM, or 1 μM to about 50 μM, or 6 μM to about 50 μM, or 1 μM to about 25 μM, or 6 μM to about 25 μM. In some embodiments zinc and the ALDC variant are added in a composition, wherein zinc is present in said composition at a concentration of 0.1 μM to about 200 mM or 1 μM to about 200 mM, or 0.1 mM to about 120 mM, such as 1 mM to about 20 mM, or 1 mM to about 10 mM, or 1 mM to 5 mM. In some embodiments zinc and the ALDC variant are added in a composition, wherein the molar ratio of zinc to ALDC variant in the composition is higher than 1 such as 2:1, or 3:1, or 5:1, or 10:1, or 20:1 or 30:1, or 50:1, or 60:1.

In some embodiments, the metal ion is added in the maturation media during production of a fermented beverage. In some embodiments, the metal ion is added the maturation media during beer, wine, cider, perry or sake fermentation. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments, zinc is added in a maturation media during beer, wine, cider, perry or sake fermentation. In some embodiments, zinc is added at a concentration of 1 μM to about 1 mM, such as 1 μM to about 300 μM, or about 6 μM to about 300 μM, or about 1 μM to about 100 μM, or 25 μM to about 50 μM, or 30 μM to about 40 μM, or 1 μM to about 50 μM, or 6 μM to about 50 μM, or 1 μM to about 25 μM, or 6 μM to about 25 μM. In some embodiments zinc and ALDC are added in a composition, wherein zinc is present in said composition at a concentration of 0.1 μM to about 200 mM, or 1 μM to about 200 mM, or 0.25 mM to about 120 mM, such as 1 mM to about 20 mM, or 1 mM to about 10 mM, or 1 mM to about 5 mM. In some embodiments zinc and the variant ALDC enzyme are added in a composition, wherein the molar ratio of zinc to variant ALDC enzyme in the composition is higher than 1 such as 2:1, or 3:1, or 5:1, or 10:1, or 20:1 or 30:1, or 50:1, or 60:1.

In some embodiments, a method of producing acetoin is provided in the disclosure. In some embodiments, a method of decomposing acetolactate is provided in the disclosure. In some embodiments, acetolactate is decomposed to acetoin. The methods involve the step of treating a substrate with a variant ALDC and a metal ion, wherein the metal ion is present at a concentration of about 1 µM to about 200 mM, such as about 1 µM to about 500 or about 1 µM to about 300 µM, or about 6 µM to about 300 µM, or about 1 µM to about 100 µM, or about 1 µM to about 50 µM, or 6 µM to about 50 µM, or 6 µM to about 25 µM, or about 10 µM to about 150 mM, or about 20 µM to about 120 mM, or about 25 µM to about 100 mM, or about 25 µM to about 50 mM, or about 25 µM to about 20 mM, or about 25 µM to about 50 µM, or about 100 µM to about 20 mM, or about 250 µM to about 20 mM, or about 1 mM to about 20 mM, or about 1 mM to about 5 mM. In some embodiments the metal ion and the ALDC variant are added in a composition, where the metal ion is present in said composition at a concentration of 0.1 µM to about 200 mM, or 1 µM to about 200 mM, or 0.25 mM to about 120 mM, such as 1 mM to about 20 mM, or 1 mM to about 5 mM. In some embodiments the metal ion and the ALDC variant are added in a composition, wherein the molar ratio of metal ion to ALDC variant in the composition is higher than 1 such as 2:1, or 3:1, or 5:1, or 10:1, or 20:1 or 30:1, or 50:1, or 60:1. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. Thus, in some embodiments, the methods involve the step of treating a substrate with an ALDC variant and zinc, wherein said zinc is present at a concentration of about 1 µM to about 1 mM, such as 1 µM to about 300 µM, or about 6 µM to about 300 µM, or 1 µM to about 100 µM, or 6 µM to about 100 µM, or 6 µM to about 50 µM, or 6 µM to about 25 µM. In some embodiments zinc and the ALDC variant are added in a composition, where zinc is present in said composition at a concentration of 0.1 µM to about 200 mM, or 1 µM to about 200 mM, or 0.25 mM to about 120 mM, such as 1 mM to about 20 mM, or 1 mM to about 5 mM. In some embodiments zinc and the variant ALDC enzyme are added in a composition, wherein the molar ratio of zinc to variant ALDC enzyme in the composition is higher than 1 such as 2:1, or 3:1, or 5:1, or 10:1, or 20:1 or 30:1, or 50:1, or 60:1.

In some embodiments a method of producing acetoin during the production of a fermented beverage is provided in the disclosure. In some embodiments, a method of decomposing acetolactate during the production of a fermented beverage is provided in the disclosure. In some embodiments, acetolactate is decomposed to acetoin.

Fermented Products

In one aspect the present invention relates to a process for producing fermented alcoholic products with a low diacetyl content by fermentation of a carbohydrate containing substrate with a microorganism. As used herein, a fermented alcoholic product with "low diacetyl content" refers to a fermented alcoholic product (e.g. a beer, a wine, a cider, a perry or a sake) produced by fermentation of a carbohydrate containing substrate with a composition comprising ALDC variant in the presence of a metal ion (such as zinc) wherein the diacetyl levels are lower when compared to the fermented alcoholic produced by fermentation of a carbohydrate containing substrate with a composition comprising the ALDC variant in the absence of a metal ion (such as zinc) under the same fermentation conditions (e.g. same temperature and for the same length of time). Examples of fermented alcoholic products with low diacetyl content are fermented alcoholic products in which the levels of diacetyl are less than about 1 ppm and/or the diacetyl levels are below about 0.5 mg/L. In one embodiment, the diacetyl levels are less than about 0.5 ppm, or less than about 0.1 ppm, or less than about 0.05 ppm, or less than about 0.01 ppm, or less than about 0.001 ppm. In one embodiment, the diacetyl levels are about less than 0.1 mg/L, or about less than 0.05 mg/L, or about less than 0.01 mg/L or about less than 0.001 mg/L.

When carbohydrate containing substrates, such as wort (e.g. worts with low malt content) or fruit juices (such as grape juice, apple juice or pear juice), are fermented with yeast or other microorganisms, various processes take place in addition to the alcohol fermentation which may cause generation of undesired by-products, e.g., the formation of diacetyl which has a strong and unpleasant smell even in very low concentrations. Alcoholic beverages, such as beer or wine or cider or perry or sake, may thus have an unacceptable aroma and flavor if the content of diacetyl considerably exceeds certain limits, e.g., in the case of some beers about 0.1 ppm.

Formation of diacetyl is also disadvantageous in the industrial production of ethanol because it is difficult to separate diacetyl from ethanol by distillation. A particular problem arises in the preparation of absolute ethanol where ethanol is dehydrated by azeotropic distillation with benzene. Diacetyl will accumulate in the benzene phase during the azeotropic distillation which may give rise to mixtures of diacetyl and benzene which makes it difficult to recover the benzene used for the azeotropic distillation.

The conventional brewing of beer comprises fermenting the wort with a suitable species of yeast, such as *Saccharomyces cerevisae* or *Saccharomyces carlsbergensis*.

In conventional brewing, the fermentation is usually effected in two steps, a main fermentation of a duration of normally 5 to 12 days and a secondary fermentation—a so-called maturation process-which may take from up to 12 weeks. During the main fermentation most of the carbohydrates in the wort are converted to ethanol and carbon dioxide. Maturation is usually effected at a low temperature in the presence of a small residual amount of yeast. The purposes of the maturation are, inter alia, to precipitate undesirable, high molecular weight compounds and to convert undesirable compounds to compounds, such as diols, which do not affect flavor and aroma. For example, butanediol, the final product of the conversion of α-acetolactate and diacetyl in beer, is typically reported as a compound with neutral sensory characteristics. The term "fermentation media" as used herein refers to a medium comprising carbohydrate containing substrates which can be fermented by yeast or other microorganisms to produce, for example, beer or wine or cider or perry or sake. Examples of fermentation media include: wort, and fruit juices (such as grape juice, apple juice and pear juice). The term "maturation media" as used herein refers to a medium comprising carbohydrate containing substrates which have been fermented by yeast or other microorganisms to produce, for example, beer or wine or cider or perry or sake. Examples of maturation media include partially fermented wort and fruit juices (such as grape juice, apple juice and pear juice).

In some aspects, the use of a composition as described herein in beer, wine, cider, perry or sake fermentation is provided. In some embodiments, compositions comprising ALDC variants are used to decompose acetolactate during beer, wine, cider, perry or sake fermentation or maturation. Also, the use of variant ALDC derivative is also provided to decompose acetolactate during beer, wine, cider, perry or sake fermentation (or maturation).

In some embodiments, the methods of the invention are thus characterized by the treatment of a substrate with a composition comprising a variant ALDC or a variant ALDC derivative as described herein during or in continuation of a fermentation process, e.g., maturation.

Thus, in some embodiments, acetolactate is enzymatically decarboxylated to acetoin, the result being that when undesirable, the formation of diacetyl from acetolactate is avoided. In some embodiments, other enzymes are used in combination with ALDC variants for the conversion of α-acetolactate. Examples of such enzymes include, but are not limited to, acetolactate reductoisomerases or isomerases.

In some embodiments, the variant ALDC and/or variant ALDC derivative compositions described herein are used together with ordinary yeast in batch fermentation.

Instead of using the enzyme in a free state, it may be used in an immobilized state, the immobilized enzyme being added to the wort during or in continuation of the fermentation (e.g., during maturation). The immobilized enzyme may also be maintained in a column through which the fermenting wort or the beer is passed. The enzyme may be immobilized separately, or coimmobilized yeast cells and acetolactate decarboxylase may be used.

In some embodiments, the variant ALDC and/or variant ALDC derivative compositions are used during beer, wine, cider, perry or sake fermentation (or maturation) to reduce the diacetyl levels to below about 1 ppm, or about less than 0.5 ppm, or about less than 0.1 ppm, or about less than 0.05 ppm or about less than 0.01 ppm, or about less than 0.001 ppm.

In some embodiments, the variant ALDC and/or variant ALDC derivative compositions described herein are used during beer, wine, cider, perry or sake fermentation or maturation to reduce VDK content below 0.1 mg/L, or about less than 0.05 mg/L, or less than 0.01 mg/L or less than 0.001 mg/L. Total VDK refers to the amount of Diacetyl plus 2,3-pentanedione. In some embodiments, the variant ALDC and/or variant ALDC derivative compositions described herein are used during beer, wine, cider, perry or sake fermentation or maturation to reduce Total VDK content below 0.1 mg/L.

The processes of the invention can not only be used in connection with the brewing of beer, but is also suitable for the production of any suitable alcoholic beverage where a reduction in diacetyl levels or other vicinal diketones is desirable (e.g. wine, sake, cider, perry, etc.). In some embodiments, the processes of the invention can be used in the production of wine where similar advantages are obtained, in particular a reduction in the maturation period and a simplification of the process. Of special interest in this context is the use of acetolactate converting enzymes in connection with the so-called malo-lactic fermentation. This process which is affected by microorganisms as species of *Leuconostoc, Lactobacillus* or *Pediococcus* is carried out after the main fermentation of wine in order to increase the pH of the product as well as its biological stability and to develop the flavor of the wine. Moreover, it is highly desirable to carry out the fermentation since it makes possible rapid bottling and thereby improves the cash-flow of wineries substantially. Unfortunately, however, the process may give rise to off-flavors due to diacetyl, the formation of which can be reduced with the aid of acetolactate converting enzymes.

Thus, in some embodiments, the processes provide for the production of alcoholic beverages with lower content of diacetyl, wherein the time required for producing the alcoholic beverages with lower content of diacetyl is reduced by at least 10%, or at least 20% or at least 30%, or at least 40%, or at least 50%, or at least 60%, or at least 70%, or at least 80%, or at least 90% when compared to a process without the use of the variant ALDC and/or variant ALDC derivative compositions described herein. In some embodiments, the processes of the invention provide for the production of alcoholic beverages with lower content of diacetyl when compared to a process without the use of the variant ALDC and/or variant ALDC derivative compositions described herein, wherein a maturation step is completely eliminated.

In some embodiments, the variant ALDC and/or variant ALDC derivative compositions described herein are used during a fermentation process (e.g. beer, wine, cider, perry or sake fermentation), such that the time required for the fermentation process is reduced by at least 10%, or at least 20% or at least 30%, or at least 40%, or at least 50%, or at least 60%, or at least 70%, or at least 80%, or at least 90%, when compared to a process without the use of the ALDC variant and/or variant ALDC derivative compositions described herein. In some embodiments, the processes of the invention provide for the production of alcoholic beverages with lower content of diacetyl when compared to a process without the use of the variant ALDC and/or variant ALDC derivative compositions described herein, wherein a maturation step is completely eliminated.

In some embodiments, the variant ALDC and/or variant ALDC derivative compositions described herein are used during a maturation or conditioning process (e.g. beer maturation/conditioning), such that the time required for the maturation or conditioning process is reduced by at least 10%, or at least 20% or at least 30%, or at least 40%, or at least 50%, or at least 60%, or at least 70%, or at least 80%, or at least 90%, when compared to a process without the use of the variant ALDC and/or variant ALDC derivative compositions described herein. In some embodiments, the processes of the invention provide for the production of alcoholic beverages with lower content of diacetyl when compared to a process without the use of the variant ALDC and/or variant ALDC derivative compositions described herein, wherein a maturation step is completely eliminated.

Further, in some embodiments, the processes described herein can be used to advantage for industrial preparation of ethanol as fermentation products are obtained without or practically without any content of diacetyl, which simplifies the distillation process, especially in case of azeotropic for the preparation of absolute ethanol, i.e. pure anhydrous ethanol.

In some embodiments, the invention provides methods for beer, wine, cider, perry or sake production comprising adding a composition comprising an variant ALDC enzyme and metal ion to a media (such as a fermentation and/or a maturation media) for the beer, wine, cider, perry or sake so that the metal ion is present in said composition at a concentration of about 0.1 μM to about 500 μM, or about 0.1 μM to about 300 μM, or about 0.1 μM to about 50 μM, or about 1 μM to about 500 μM, or about 1 μM to about 300 μM, or about 6 μM to about 300 μM, or about 1 μM to about 100 μM, or about 1 μM to about 50 μM, or about 6 μM to about 50 μM, or about 6 μM to about 25 μM, or about 10 μM to about 150 mM, or about 20 µM to about 120 mM, or about 25 µM to about 100 mM, or about 25 µM to about 50 mM, or about 25 µM to about 20 mM, or about 25 µM to about 50 µM, or about 100 µM to about 20 mM, or about 250 µM to about 20 mM, or about 1 mM to about 20 mM, or about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$.

In some embodiments, the invention provides methods for beer, wine, cider, perry or sake production comprising adding a composition comprising a variant ALDC (enzyme) and metal ion to a media (such as a fermentation and/or a maturation media) for the beer, wine, cider, perry or sake, wherein the metal ion is present in said composition at a concentration of about 1 µM to about 200 mM, or about 100 µM to about 200 mM, and the composition comprising the variant ALDC and the metal ion are added at a concentration of about 0.01 g to about 10 g per hectoliter of beer, wine, cider, perry or sake ferment. In some embodiments, methods for beer, wine, cider, perry or sake production are provided comprising adding a composition comprising variant ALDC and metal ion to a media (such as a fermentation and/or a maturation media) for the beer, wine, cider, perry or sake, wherein the metal ion is present in said composition at a concentration of about 1 µM to about 200 mM, or about 100 µM to about 200 mM, and the composition comprising the variant ALDC enzyme and the metal ion are added at a concentration of about 0.5 g to about 10 g per hectoliter of beer, wine, cider, perry or sake ferment. In some embodiments, the invention provides methods for beer, wine, cider, perry or sake production comprising adding a composition comprising a variant ALDC enzyme and metal ion to a media (such as a fermentation and/or a maturation media) for the beer, wine, cider, perry or sake, wherein the metal ion is present in said composition at a concentration of about 1 µM to about 200 mM or about 100 µM to about 200 mM, and the composition comprising the variant ALDC enzyme and the metal ion are added at a concentration of about 1 g to about 5 g per hectoliter of beer, wine, cider, perry or sake ferment. In some embodiments, the invention provides methods for beer, wine, cider, perry or sake production comprising adding a composition comprising a variant ALDC enzyme and metal ion to a media (such as a fermentation and/or a maturation media) for the beer, wine, cider, perry or sake, wherein the metal ion is present in said composition at a concentration of about 1 µM to about 200 mM, or about 100 µM to about 200 mM, and the composition comprising the variant ALDC enzyme and the metal ion are added at a concentration of about 1 g to about 2 g per hectoliter of beer, wine, cider, perry or sake ferment. In some embodiments the metal ion is present in the composition at a concentration of about 1 mM to about 20 mM, or about 1 mM to about 10 mM, or about 1 mM to about 5 mM. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said variant ALDC enzyme is in the range of 950 to 3500 Units per mg of protein or 1000 to 3500 Units per mg of protein or 1500 to 3500 Units per mg of protein.

In some embodiments, the invention provides methods for beer, wine, cider, perry or sake production comprising adding a variant ALDC enzyme and metal ion in a composition to a media (such as a fermentation and/or a maturation media) for the beer, wine, cider, perry or sake, wherein the molar ratio of the metal ion to the variant ALDC enzyme is higher than 1, and the composition comprising the variant ALDC enzyme and the metal ion are added at a concentration of about 0.01 g to about 10 g per hectoliter of beer, wine, cider, perry or sake ferment. In some embodiments, the invention provides methods for beer, wine, cider, perry or sake production comprising adding a variant ALDC enzyme and metal ion in a composition to a media (such as a fermentation and/or a maturation media) for the beer, wine, cider, perry or sake, wherein the molar ratio of the metal ion to the variant ALDC e is higher than 1, and the composition comprising the variant ALDC and the metal ion are added at a concentration of about 0.5 g to about 10 g per hectoliter of beer, wine, cider, perry or sake ferment. In some embodiments, methods are provided for beer, wine, cider, perry or sake production comprising adding a variant ALDC enzyme and metal ion in a composition to a media (such as a fermentation and/or a maturation media) for the beer, wine, cider, perry or sake, wherein the molar ratio of the metal ion to the variant ALDC enzyme is higher than 1, and the composition comprising the variant ALDC enzyme and the metal ion are added at a concentration of about 1 g to about 5 g per hectoliter of beer, wine, cider, perry or sake ferment. In some embodiments, methods are provided for beer, wine, cider, perry or sake production comprising adding a variant ALDC enzyme and metal ion in a composition to a media (such as a fermentation and/or a maturation media) for the beer, wine, cider, perry or sake, wherein the molar ratio of the metal ion to the variant ALDC enzyme is higher than 1, and the composition comprising the variant ALDC enzyme and the metal ion are added at a concentration of about 1 g to about 2 g per hectoliter of beer, wine, cider, perry or sake ferment. In some embodiments, the molar ratio of the metal ion to the variant ALDC enzyme is 2:1, or 3:1, or 5:1, or 10:1, or 20:1 or 30:1, or 50:1, or 60:1, or higher. In some embodiments, the metal ion is selected from the group consisting of $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said variant ALDC is in the range of 950 to 3500 Units per mg of protein or 1000 to 35000 Units per mg of protein or 1500 to 3500 Units per mg of protein.

Production of ALDC Enzymes

In one aspect, the description relates to a nucleic acid capable of encoding a variant ALDC (enzyme) as described herein. In a further aspect, the description relates to an expression vector or plasmid comprising such a nucleic acid, or capable of expressing the enzyme as described herein. In one aspect, the expression vector or plasmid comprises a promoter derived from *Trichoderma* such as a *T. reesei* cbhI-derived promoter. In a further aspect, the expression vector or plasmid comprises a terminator derived from *Trichoderma* such as a *T. reesei* cbhI-derived terminator. In yet a further aspect, the expression vector or plasmid comprises one or more selective markers such as *Aspergillus nidulans* amdS and pyrG. In another aspect, the expression vector or plasmid comprises one or more telomere regions allowing for a non-chromosomal plasmid maintenance in a host cell.

In one aspect, the description relates to a host cell having heterologous expression of an enzyme as herein described. In a further aspect, the host cell is a fungal cell. In yet a further aspect, the fungal cell is of the genus *Trichoderma*. In yet a further aspect, the fungal cell is of the species *Trichoderma reesei* or of the species *Hypocrea jecorina*. In another aspect, the host cell comprises, preferably is transformed with, a plasmid or an expression vector as described herein.

In some embodiments, the host cell is a bacterial host cell such as *Bacillus*. In some embodiments the enzyme is produced by cultivation of a *Bacillus subtilis* strain containing a gene encoding and expressing a variant ALDC as described herein. Examples of such host cells and cultivation thereof are described in DK149335B.

Examples of suitable expression and/or integration vectors are provided in Sambrook et al. (1989) supra, and Ausubel (1987) supra, and van den Hondel et al. (1991) in Bennett and Lasure (Eds.) *More Gene Manipulations In Fungi*, Academic Press pp. 396-428 and U.S. Pat. No. 5,874,276. Reference is also made to the Fungal Genetics Stock Center Catalogue of Strains (FGSC, www.fgsc.net) for a list of vectors. Particularly useful vectors include vectors obtained from for example Invitrogen and Promega. Suitable plasmids for use in bacterial cells include pBR322 and pUC19 permitting replication in *E. coli* and pE194 for example permitting replication in *Bacillus*. Other specific vectors suitable for use in *E. coli* host cells include vectors such as pFB6, pBR322, pUC18, pUC100, pDONR™ 201, 10 pDONR™ 221, pENTR™, pGEM® 3Z and pGEM® 4Z.

Specific vectors suitable for use in fungal cells include pRAX, a general purpose expression vector useful in *Aspergillus*, pRAX with a glaA promoter, and in *Hypocrea/Trichoderma* includes pTrex3g with a cbh1 promoter.

In some embodiments, the host cells are fungal cells and optionally filamentous fungal host cells. The term "filamentous fungi" refers to all filamentous forms of the subdivision Eumycotina (see, Alexopoulos, C. J. (1962), *Introductory Mycology*, Wiley, New York). These fungi are characterized by a vegetative mycelium with a cell wall composed of chitin, cellulose, and other complex polysaccharides. The filamentous fungi of the present disclosure are morphologically, physiologically, and genetically distinct from yeasts. Vegetative growth by filamentous fungi is by hyphal elongation and carbon catabolism is obligatory aerobic. In the present disclosure, the filamentous fungal parent cell may be a cell of a species of, but not limited to, *Trichoderma* (e.g., *Trichoderma reesei*, the asexual morph of *Hypocrea jecorina*, previously classified as *T. longibrachiatum, Trichoderma viride, Trichoderma koningii, Trichoderma harzianum*) (Sheir-Neirs et al., *Appl. Microbiol. Biotechnol.* 20:46-53 (1984); ATCC No. 56765 and ATCC No. 26921), *Penicillium* sp., *Humicola* sp. (e.g., *H. insolens, H. lanuginosa* and *H. grisea*), *Chrysosporium* sp. (e.g., *C. lucknowense*), *Gliocladium* sp., *Aspergillus* sp. (e.g., *A. oryzae, A. niger, A sojae, A. japonicus, A. nidulans*, and *A. awamori*) (Ward et al., *Appl. Microbiol. Biotechnol.* 39:738-743 (1993) and Goedegebuur et al., *Curr. Genet.* 41:89-98 (2002)), *Fusarium* sp., (e.g., *F. roseum, F. graminum, F. cerealis, F. oxysporum*, and *F. venenatum*), *Neurospora* sp., (*N. crassa*), *Hypocrea* sp., *Mucor* sp. (*M. miehei*), *Rhizopus* sp., and *Emericella* sp. (see also Innis et al., *Science* 228: 21-26 (1985)). The term "*Trichoderma*" or "*Trichoderma* sp." or "*Trichoderma* spp." refer to any fungal genus previously or currently classified as *Trichoderma*.

In some embodiments, the host cells will be gram-positive bacterial cells. Non-limiting examples include strains of *Streptomyces* (e.g., *S. lividans, S. coelicolor*, and *S. griseus*) and *Bacillus*. As used herein, "the genus *Bacillus*" includes all species within the genus "*Bacillus*," as known to those of skill in the art, including, but not limited to, *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus tearothermophilus.*"

In some embodiments, the host cell is a gram-negative bacterial strain, such as *E. coli* or *Pseudomonas* sp. In other embodiments, the host cells may be yeast cells such as *Saccharomyces* sp., *Schizosaccharomyces* sp., *Pichia* sp., or *Candida* sp. In other embodiments, the host cell will be a genetically engineered host cell wherein native genes have been inactivated, for example by deletion in bacterial or fungal cells. Where it is desired to obtain a fungal host cell having one or more inactivated genes known methods may be used (e.g., methods disclosed in U.S. Pat. Nos. 5,246,853, 5,475,101, and WO 92/06209). Gene inactivation may be accomplished by complete or partial deletion, by insertional inactivation or by any other means that renders a gene nonfunctional for its intended purpose (such that the gene is prevented from expression of a functional protein). In some embodiments, when the host cell is a *Trichoderma* cell and particularly a *T. reesei* host cell, the cbh1, cbh2, eg/1 and eg/2 genes will be inactivated and/or deleted. Exemplary *Trichoderma reesei* host cells having quad-deleted proteins are set forth and described in U.S. Pat. No. 5,847,276 and WO 05/001036. In other embodiments, the host cell is a protease deficient or protease minus strain. The term "protease deficient" or a "protease minus strain" as used herein refers to a host cell derived or derivable from a parental cell wherein the host cell comprises one or more genetic alterations that causes the host cells to produce a decreased amount of one or more proteases (e.g. functional proteases) when compared to the parental cell; preferably said host cell is deficient in one or more proteases selected from the group consisting of WprA, Vpr, Epr, IspA, Bpr, NprE, AprE, ampS, aprX, bpf, clpCP, clpEP, clpXP, codWX, lonA, lonB, nprB, map, mlpA, mpr, pepT, pepF, dppA, yqyE, tepA, yfiT, yflG, ymfF, ypwA, yrrN, yrrO, and ywaD. A variant host cell derived from a parental cell is provided, the variant host cell comprises one or more genetic alterations that causes cells of the variant strain to produce a decreased amount of one or more proteases when compared to the parental cell.

Introduction of a DNA construct or vector into a host cell includes techniques such as transformation; electroporation; nuclear microinjection; transduction; transfection, (e.g., lipofection-mediated and DEAE-Dextrin mediated transfection); incubation with calcium phosphate DNA precipitate; high velocity bombardment with DNA-coated microprojectiles; and protoplast fusion. General transformation techniques are known in the art (see, e.g., Ausubel et al. (1987) supra, chapter 9; and Sambrook et al. (1989) supra, and Campbell et al., *Curr. Genet.* 16:53-56 (1989)).

Transformation methods for *Bacillus* are disclosed in numerous references including Anagnostopoulos C. and J. Spizizen, *J. Bacteriol.* 81:741-746 (1961) and WO 02/14490.

Transformation methods for *Aspergillus* are described in Yelton et al., *Proc. Natl. Acad. Sci. USA* 81:1470-1474 (1984); Berka et al., (1991) in *Applications of Enzyme Biotechnology*, Eds. Kelly and Baldwin, Plenum Press (NY); Cao et al., *Protein Sci.* 9:991-1001 (2000); Campbell et al., *Curr. Genet.* 16:53-56 (1989), and EP 238 023. The expression of heterologous protein in *Trichoderma* is described in U.S. Pat. Nos. 6,022,725; 6,268,328; Harkki et al. *Enzyme Microb. Technol.* 13:227-233 (1991); Harkki et al., *BioTechnol.* 7:596-603 (1989); EP 244,234; EP 215,594; and Nevalainen et al., "The Molecular Biology of *Trichoderma* and its Application to the Expression of Both Homologous and Heterologous Genes", in *Molecular Industrial Mycology*, Eds. Leong and Berka, Marcel Dekker Inc., NY (1992) pp. 129-148). Reference is also made to WO96/00787 and Bajar et al., *Proc. Natl. Acad. Sci. USA* 88:8202-8212 (1991) for transformation of *Fusarium* strains.

In one aspect, the description relates to a method of isolating a variant ALDC as defined herein, the method comprising the steps of inducing synthesis of the variant ALDC in a host cell as defined herein having heterologous expression of said variant ALDC and recovering extracellular protein secreted by said host cell, and optionally purifying the enzyme. In a further aspect, the description relates to a method for producing an enzyme as defined herein, the method comprising the steps of inducing synthesis of the enzyme in a host cell as defined herein having heterologous expression of said enzyme, and optionally purifying the enzyme. In a further aspect, the description relates to a method of expressing an enzyme as defined herein, the method comprising obtaining a host cell as defined herein, or any suitable host cells as known by a person of ordinary skill in the art, and expressing the enzyme from said host cell, and optionally purifying the enzyme. In another aspect, the enzyme as defined herein is the dominant secreted protein.

In some embodiments, metal ions such as $Zn^{2+}$, $Mg^{2+}$, $Mn^{2+}$, $Co^{2+}$, $Cu^{2+}$, $Ba^{2+}$, $Ca^{2+}$ and $Fe^{2+}$ and combinations thereof are added to the media (such as a cultivation and/or a fermentation and/or a maturation media) during and/or after enzyme production to increase the recovered yields from microorganisms.

In some embodiments, the invention provides a cultivation media for an ALDC variant-producing host cell comprising a metal ion at a concentration of about 1 µM to about 1 mM. In some embodiments, the invention provides a cultivation media for an ALDC variant-producing host cell comprising a metal ion at a concentration of about 25 µM to about 150 µM. In some embodiments, the invention provides a cultivation media for an ALDC variant-producing host cell comprising a metal ion at a concentration of about 25 µM to about 50 µM. In some embodiments, the invention provides a cultivation media for an ALDC variant-producing host cell comprising a metal ion at a concentration of about 30 µM to about 40 µM. In some embodiments, the invention provides a cultivation media for an ALDC variant-producing host cell comprising a metal ion at a concentration of about 40 µM to about 150 µM. In some embodiments, the invention provides a cultivation media for an ALDC variant-producing host cell comprising a metal ion at a concentration of about 60 µM to about 150 µM. In some embodiments, the metal ion is selected from the group consisting of $Zn^{2+}$, $Mg^{2+}$, $Mn^{2+}$, $Co^{2+}$, $Cu^{2+}$, and $Fe^{2+}$ and combinations thereof. In some embodiments, the metal ion is selected from the group consisting of $Zn^{2+}$, $Cu^{2+}$, and $Fe^{2+}$. In some embodiments, the metal ion is selected from the group consisting of $Zn^{2+}$, $Mn^{2+}$, and $Co^{2+}$. In some embodiments, the metal ion is $Zn^{2+}$ or $Mn^{2+}$. In some embodiments, the metal ion is $Zn^{2+}$. In some embodiments, the activity of said variant ALDC is in the range of 950 to 2500 Units per mg of protein or 1000 to 2500 Units per mg of protein or 1500 to 2500 Units per mg of protein. The term "ALDC variant-producing host cell" as used herein refers to a (recombinant) host cell capable of expressing at least one variant ALDC (as described herein) when said host cell is cultured under conditions permitting the expression of the nucleic acid sequence encoding the variant ALDC. The nucleic acid sequence encoding the ALDC variant may be heterologous or homologous to the host cell. In some embodiments, the ALDC variant-producing host cell is *Bacillus subtilis*. In some embodiments, the ALDC variant-producing host cell is *Bacillus subtilis* comprising a gene encoding and expressing the present variant ALDC wherein the variant ALDC comprises an amino acid sequence having at least 80%, 85%, 90%, 95%, 97%, 98%, 99% or 100% identity with SEQ ID SEQ ID NO: 3, and wherein the polypeptide comprises at least one amino acid substitution at position 62 with reference to the position numbering of the sequence shown in SEQ ID NO: 3, or any functional fragment thereof. In some embodiments, the ALDC variant-producing host cell is *Bacillus subtilis* comprising a nucleic acid sequence encoding the variant ALDC wherein said nucleic acid sequence encoding the variant ALDC has at least 80%, 85%, 90%, 95%, 97%, 98%, 99% or 100% identity with SEQ ID NO: 6 or any functional fragment thereof. In some embodiments, the ALDC variant-producing host cell is *Bacillus subtilis* comprising a gene encoding the ALDC variant having the amino acid sequence SEQ ID NO: 8 (mature protein).

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

Example 1

Heterologous Expression of Acetolactate Decarboxylase, aldB

The *Brevibacillus brevis* (which may be referred to as *Bacillus brevis*) acetolactate decarboxylases (ALDC) aldB gene was previously identified (Diderichsen et al., *J Bacteriol.* (1990) 172(8): 4315), with the sequence set forth as UNIPROT Accession No. P23616.1. The sequence of this gene, aldB, is depicted in SEQ ID NO:1. The nucleotides highlighted in bold and underlined are the nucleotides which encode the signal peptide. The aldB gene and corresponding encoded proenzyme are also referred to as the wildtype (WT).

SEQ ID NO: 1 sets forth the nucleotide sequence
of the aldB gene:
<u>atgaaaaaaaatatcatcacttctatcacatctctggctctggttgccg</u>

<u>ggctgctttgactgcttttgca</u>gctacaacggctactgtaccagcacca cctgccaagcaggaatccaaacctgcggttgccgctaatccggcaccaa -continued aaaatgtactgtttcaatactcaacgatcaatgcactcatgcttggaca gtttgaaggggacttgactttgaaagacctgaagctgcgaggcgatatg gggcttggtaccatcaatgatctcgatggagagatgattcagatgggta caaaattctaccagatcgacagcaccggaaaattatcggagctgccaga aagtgtgaaaactccatttgcggttactacacatttcgagccgaaagaa aaaactacattaaccaatgtgcaagattacaatcaattaacaaaaatgc ttgaggagaaatttgaaaacaagaacgtcttttatgccgtaaagctgac cggtacctttaagatggtaaaggctagaacagttccaaaacaaaccaga ccttatccgcagctgactgaagtaaccaaaaaacaatccgagtttgaat ttaaaaatgttaagggaaccctgattggettctatacgccaaattatgc agcagccctgaatgttcccggattccatctccacttcatcacagaggat aaaacaagtggcggacacgtattaaatctgcaatttgacaacgcgaatc tggaaatttctccgatccatgagtttgatgtacaattgccgcacacaga tgattttgcccactctgatctgacacaagttactactagccaagtacac caagctgagtcagaaagaaaataa The proenzyme encoded by the aldB gene is depicted in SEQ ID NO: 2. At the N-terminus, the protein has a signal peptide with a length of 24 amino acids as predicted by SignalP-NN (Emanuelsson et al., *Nature Protocols* (2007) 2: 953-971). This signal peptide sequence is underlined and is in bold in SEQ ID NO:2. The presence of a signal peptide indicates that this acetolactate decarboxylase, aldB is a secreted enzyme. The sequence of the predicted, fully processed mature chain (aldB, 261 amino acids) is depicted in SEQ ID NO: 3.

SEQ ID NO: 2 sets forth the amino acid sequence
of the ace tolactate decarboxylase (ALDC)
precursor aldB:
MKKNIITSITSLALVAGLSLTAFAATTATVPAPPAKQESKPAVAANPAP

KNVLFQYSTINALMLGQFEGDLTLKDLKLRGDMGLGTINDLDGEMIQMG

TKFYQIDSTGKLSELPESVKTPFAVTTHFEPKEKTTLTNVQDYNQLTKM

LEEKFENKNVFYAVKLTGTFKMVKARTVPKQTRPYPQLTEVTKKQSEFE

FKNVKGTLIGFYTPNYAAALNVPGFHLHFITEDKTSGGHVLNLQFDNAN

LEISPIHEFDVQLPHTDDFAHSDLTQVTTSQVHQAESERK

SEQ ID NO: 3 sets forth the predicted amino acid
sequence of the mature acetolactate decarboxylase
(ALDC) aldB (261 amino acids):
ATTATVPAPPAKQESKPAVAANPAPKNVLFQYSTINALMLGQFEGDLTL

KDLKLRGDMGLGTINDLDGEMIQMGTKFYQIDSTGKLSELPESVKTPFA

VTTHFEPKEKTTLTNVQDYNQLTKMLEEKFENKNVFYAVKLTGTFKMVK

ARTVPKQTRPYPQLTEVTKKQSEFEFKNVKGTLIGFYTPNYAAALNVPG

FHLHFITEDKTSGGHVLNLQFDNANLEISPIHEFDVQLPHTDDFAHSDL

TQVTTSQVHQAESERK

Figure 2:
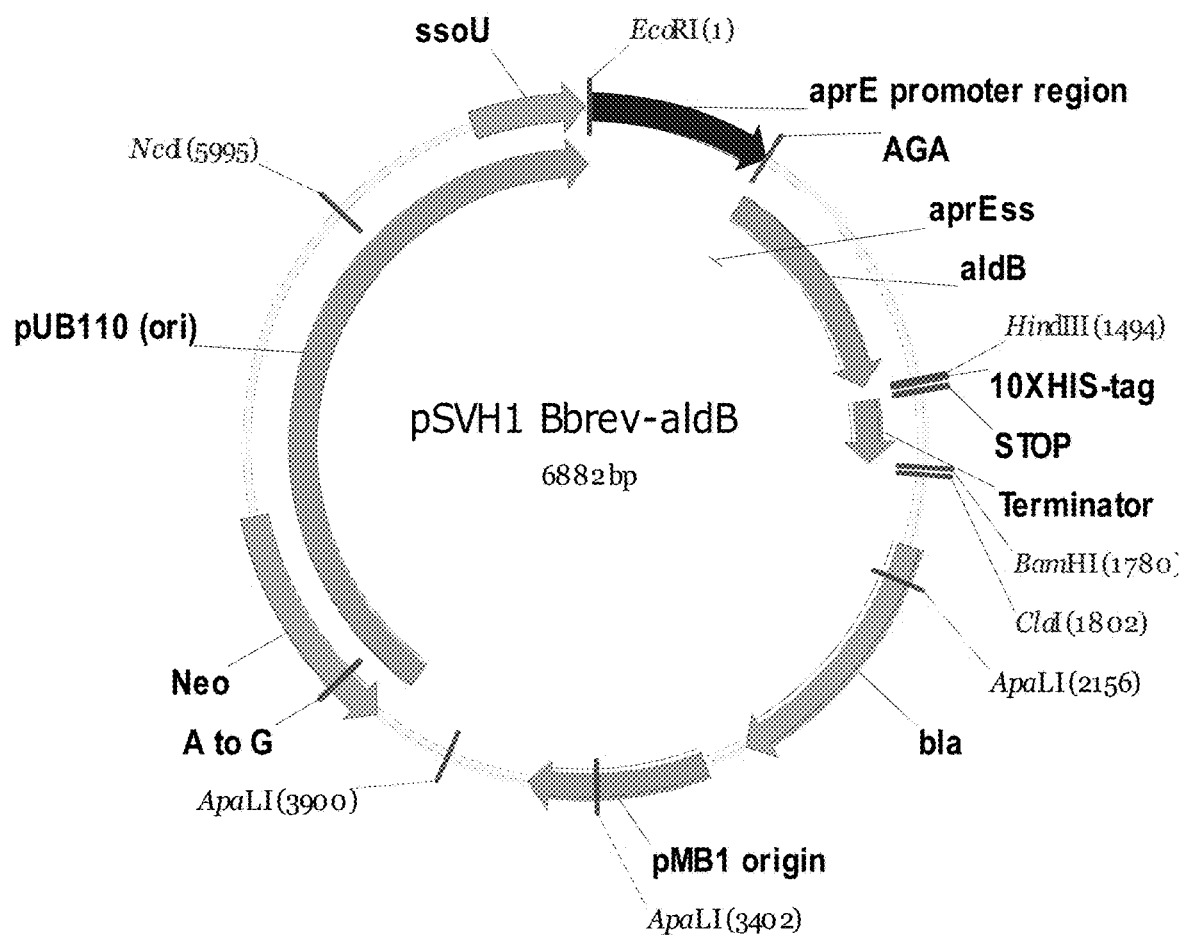
FIG. 2 shows a plasmid map of pSVH1_Bbrev_aldB for expression of acetolactate decarboxylase, aldB.
Figure 3:
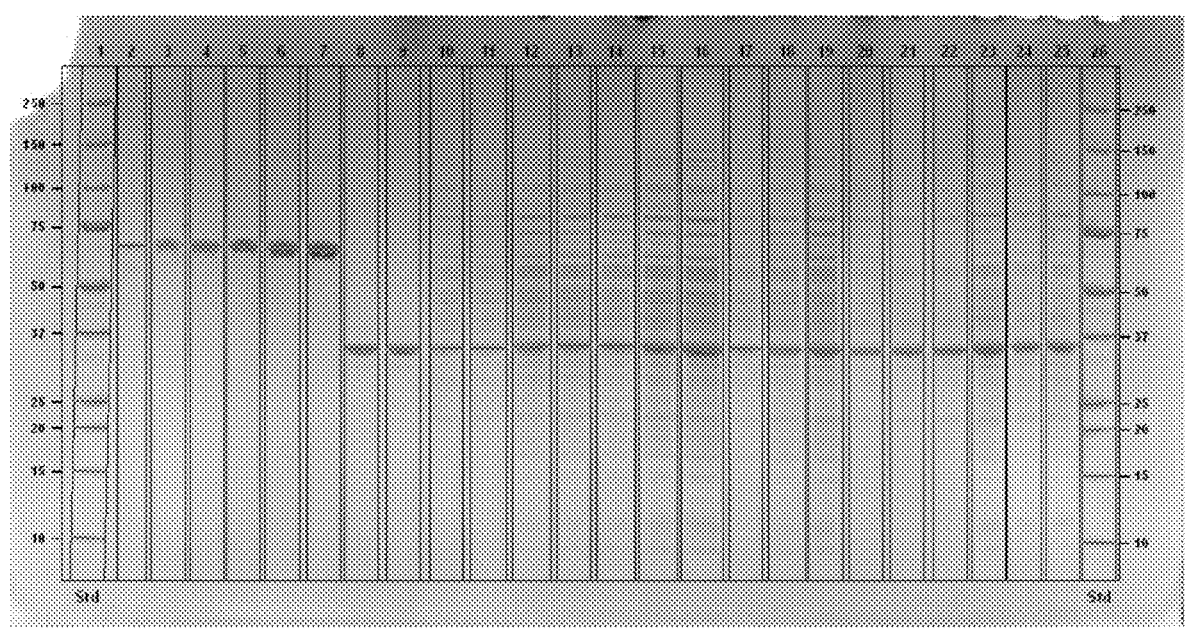
FIG. 3 shows SDS-PAGE with variants of aldB expressed in a *Bacillus subtilis* strain. Lane: 1 and 26) Molecular weight marked, Lane 2-7) BSA standard, Lane 8-9) Purified aldB, Lane 10-16) aldB-T62A, Lane 17-19) aldB-T62A w. 50% glycerol, Lane 19-22) aldB and Lane 23-25 aldB w. 50% glycerol. Standards and aldB variants are marked with a pink line.

The aldB gene that encodes an acetolactate decarboxylases enzyme (ALDC) was produced in *B. subtilis* using the synthetic gene inserted into the pSVH1 vector, see FIG. 1. The position of the aldB gene containing the aldB signal sequence was after the "aprE promoter region" with additional "AGA" at 5' end. For expression the pSVH1_Bbrev_aldB vector was transformed into an appropriate *B. subtilis* strain. A map of the pSVH1 vector containing the aldB gene (pSVH1_Bbrev_aldB) is shown in FIG. 2.

To produce aldB, a *B. subtilis* strain transformant containing pSVH1_Bbrev_aldB was cultured in 15-mL Falcon tubes for 16 hours in TSB (broth) with 10 ppm neomycin, and 300 µL of this pre-culture was added to a 500-mL flask filled with 30 mL of cultivation media (described below) supplemented with 10 ppm neomycin. The flasks were incubated for 24, 48 and 72 hours at 33° C. with constant rotational mixing at 180 rpm. Cultures were harvested by centrifugation at 14500 rpm for 20 minutes in conical tubes. The culture supernatants were used for protein determination and assays. The cultivation media was an enriched semi-defined media based on MOPs buffer, with urea as major nitrogen source, glucose as the main carbon source, 50 µM $ZnSO_4$ to ensure high enzyme activity and supplemented with 1% soytone for robust cell growth.

The nucleotide mature sequence of the aldB gene in plasmid pSVH1_Bbrev_aldB is depicted in SEQ ID NO:4 gctacaacggctactgtaccagcaccacctgccaagcaggaatccaaac ctgcggttgccgctaatccggcaccaaaaaatgtactgtttcaatactc aacgatcaatgcactcatgcttggacagtttgaaggggacttgactttg aaagacctgaagctgcgaggcgatatgggggcttggtaccatcaatgatc tcgatggagagatgattcagatgggtacaaaattctaccagatcgacag caccggaaaattatcggagctgccagaaagtgtgaaaactccatttgcg gttactacacatttcgagccgaaagaaaaaactacattaaccaatgtgc aagattacaatcaattaacaaaaatgcttgaggagaaatttgaaaacaa gaacgtcttttatgccgtaaagctgaccggtacttttaagatggtaaag gctagaacagttccaaaacaaaccagaccttatccgcagctgactgaag taaccaaaaaacaatccgagtttgaatttaaaaatgttaagggaaccct gattggcttctatacgccaaattatgcagcagccctgaatgttcccgga ttccatctccacttcatcacagaggataaaacaagtggcggacacgtat taaatctgcaatttgacaacgcgaatctggaaatttctccgatccatga gtttgatgttcaattgccgcacacagatgattttgcccactctgatctg acacaagttactactagccaagtacaccaagctgagtcagaaagaaaa The amino acid sequence of the aldB precursor protein expressed from plasmid pSVH1_Bbrev_aldB is depicted in SEQ ID NO:5

*vrskklwisllfaltliftmafsnmsaqa*ATTATVPAPPAKQESKPAVA

ANPAPKNVLFQYSTINALMLGQFEGDLTLKDLKLRGDMGLGTINDLDGE

MIQMGTKFYQIDSTGKLSELPESVKTPTTHFEPKEKTTLTNVQDYNQLT

KMLEEKFENKNVFYAVKLTGTFKMVKARTVPKQTRPYPQLTEVTKKQSE

FEFKNVKGTLIGFYTPNYAAALNVPGFHLHFITEDKTSGGHVLNLQFDN

ANLEISPIHEFDVQLPHTDDFAHSDLTQVTTSQVHQAESERK

The aldB gene variant encoding acetolactate decarboxylases enzyme (ALDC) variant with the amino acid substitution Threonine to Alanine at position 62 (T62A) was produced as a synthetic gene and inserted into the pSVH1 vector as described above for the wildtype aldB gene.

The nucleotide sequence of the aldB_T62A variant gene in plasmid pSVH1_Bbrev_aldB_T62A is depicted in SEQ ID NO:6

<u>gtgagaagcaaaaaattgtggatcagcttgttgtttgcgttaacgttaa</u>

<u>tctttacgatggcgttcagcaacatgagcgcgcaggct</u>gctacaacggc tactgtaccagcaccacctgccaagcaggaatccaaacctgcggttgcc gctaatccggcaccaaaaaatgtactgtttcaatactcaacgatcaatg cactcatgcttggacagtttgaaggggacttgactttgaaagacctgaa gctgcgaggcgatatgggcttggtgcaatcaatgatctcgatggagag atgattcagatgggtacaaaattctaccagatcgacagcaccggaaaat tatcggagctgccagaaagtgtgaaaactccatttgcggttactacaca tttcgagccgaaagaaaaaactacattaaccaatgtgcaagattacaat caattaacaaaaatgcttgaggagaaatttgaaaacaagaacgtcttt atgccgtaaagctgaccggtactttaagatggtaaaggctagaacagt tccaaaacaaaccagaccttatccgcagctgactgaagtaaccaaaaaa caatccgagtttgaatttaaaaatgttaagggaaccctgattggcttct atacgccaaattatgcagcagccctgaatgttcccggattccatctcca cttcatcacagaggataaaacaagtggcggacacgtattaaatctgcaa tttgacaacgcgaatctggaaattctccgatccatgagtttgatgttc aattgccgcacacagatgattttgcccactctgatctgacacaagttac tactagccaagtacaccaagctgagtcagaaagaaaataa The amino acid sequence of the aldB_T62A variant precursor protein expressed from plasmid pSVH1_Bbrev_aldB_T62A is depicted in SEQ ID NO:7

<u>VRSKKLWISLLFALTLIFTMAFSNMSAQA</u>ATTATVPAPPAKQESKPAVA

ANPAPKNVLFQYSTINALMLGQFEGDLTLKDLKLRGDMGLGAINDLDGE

MIQMGTKFYQIDSTGKLSELPESVKTPFAVTTHFEPKEKTTLTNVQDYN

QLTKMLEEKFENKNVFYAVKLTGTFKMVKARTVPKQTRPYPQLTEVTKK

QSEFEFKNVKGTLIGFYTPNYAAALNVPGFHLHFITEDKTSGGHVLNLQ

FDNANLEISPIHEFDVQLPHTDDFAHSDLTQVTTSQVHQAESERK

```
SEQ ID NO: 8 sets forth the predicted amino acid
sequence of the mature acetolactate decarboxylase
variant aldB_T62A (261 amino acids):
```
ATTATVPAPPAKQESKPAVAANPAPKNVLFQYSTINALMLGQFEGDLTL

KDLKLRGDMGLGAINDLDGEMIQMGTKFYQIDSTGKLSELPESVKTPFA

VTTHFEPKEKTTLTNVQDYNQLTKMLEEKFENKNVFYAVKLTGTFKMVK

ARTVPKQTRPYPQLTEVTKKQSEFEFKNVKGTLIGFYTPNYAAALNVPG

FHLHFITEDKTSGGHVLNLQFDNANLEISPIHEFDVQLPHTDDFAHSDL

TQVTTSQVHQAESERK.

Small Scale Culture Conditions

To produce aldB, a *B. subtilis* strain transformant containing aldB expression cassette was cultured in 15-mL Falcon tubes for 5 hours in TSB (broth) with 10 ppm neomycin, and 300 μL of this pre-culture was added to a 500-mL flask filled with 30 mL of cultivation media (described below) supplemented with 10 ppm neomycin and 50 μM $Zn^{2+}$. The flasks were incubated for 24, 48 and 72 hours at 33° C. with constant rotational mixing at 180 rpm. Cultures were harvested by centrifugation at 14500 rpm for 20 minutes in conical tubes. The culture supernatants were used for protein determination and assays. The cultivation media was an enriched semi-defined media based on MOPs buffer, with urea as major nitrogen source, maltrin as the main carbon source.

Fed-Batch Fermentation Conditions

To produce aldB, a *B. subtilis* strain transformant containing aldB expression cassette was cultured in a 250-mL flasks containing 30 mL of complex medium with 10 ppm neomycin. The flask was incubated for 6 hours at 37° C. with constant rotational mixing at 180 rpm.

The culture was transferred to a stirred fermentor containing 7 liters of sterilized media components as described in Table 1 below. Temperature was controlled to 37° C.; pH was controlled to 7.5 using ammonium hydroxide as alkaline titrant; dissolved oxygen was maintained at 40% or higher by maintaining an airflow of 7 liters/min, a constant overpressure of 1 bar and adjusting stirring rate. When initial glucose was exhausted a feeding profile feeding a 60% glucose solution into the fermentor was initiated (initial feeding rate was 20 g/h linearly increasing to 32.8 g/h over 7 hours and kept constant at that rate until fermentation termination).

Total fermentation time was 44 hours.

TABLE 1

| Media recipe for ALDC fermentation | |
|---|---|
| Component | Recipe Conc (g/kg) |
| Soy Meal | 50.0 |
| Citric acid | 0.10 |
| Magnesium sulfate heptahydrate | 2.29 |
| Potassium Phosphate, Mono Basic | 5.44 |
| Ferrous sulfate, heptahydrate | 0.029 |
| Manganese Sulfate Mono hydrate | 0.051 |
| Zinc sulphate heptahydrate | 0.001 |
| Glucose mono hydrate | 1.10 |
| Anti foam agent | 3.00 |

Example 2

Protein Determination Methods

Protein Determination by Stain Free Imager Criterion

Protein was quantified by SDS-PAGE gel and densitometry using Gel Doc™ EZ imaging system. Reagents used in the assay: Concentrated (2×) Laemmli Sample Buffer (Bio-Rad, Catalogue #161-0737); 26-well XT 4-12% Bis-Tris Gel (Bio-Rad, Catalogue #345-0125); protein markers "Precision Plus Protein Standards" (Bio-Rad, Catalogue #161-0363); protein standard BSA (Thermo Scientific, Catalogue #23208) and SimplyBlue Safestain (Invitrogen, Catalogue #LC 6060. The assay was carried out as follow: In a 96-well PCR plate 50 μL diluted enzyme sample were mixed with 50 μL sample buffer containing 2.7 mg DTT. The plate was sealed by Microseal 'B' Film from Bio-Rad and was placed into PCR machine to be heated to 70° C. for 10 minutes. After that the chamber was filled by running buffer, gel cassette was set. Then 10 μL of each sample and standard (0.125-1.00 mg/mL BSA) was loaded on the gel and 5 μL of the markers were loaded. After that the electrophoresis was run at 200 V for 45 min. Following electrophoresis, the gel was rinsed 3 times for 5 min in water, then stained in Safestain overnight and finally destained in water. Then the gel was transferred to Imager. Image Lab software was used for calculation of intensity of each band. By knowing the protein amount of the standard sample, the calibration curve can be made. The amount of sample can be determined by the band intensity and calibration curve. The protein quantification method was employed to prepare samples of aldB acetolactate decarboxylases enzyme used for assays shown in subsequent Examples.

Example 3

Activity Assay Method

Spectrophotometric Assay of α-Acetolactate Decarboxylase

α-Acetolactate decarboxylase (ALDC) catalyses the decarboxylation of α-acetolactate to acetoin. The reaction product acetoin can be quantified colourimetrically. Acetoin mixed with α-naphtol and creatine forms a characteristic red color absorbing at $OD_{522\ nm}$. ALDC activity was calculated based on $OD_{522\ nm}$ and an acetoin calibration curve. The assay was carried out as follows: 20 mM acetolactate substrate was prepared by mixing 100 µL ethyl-2-acetoxy-2-methylacetoacetate (Sigma, Catalogue #220396) with 3.6 mL 0.5 M NaOH at 10° C. for 10 min. 20 mL 50 mM MES pH 6.0 was added, pH was adjusted to pH 6.0 and volume adjusted to 25 mL with 50 mM MES pH 6.0. 80 µL 20 mM acetolactate substrate was mixed with 20 µL enzyme sample diluted in 50 mM MES, pH 6.0, 0.6 M NaCl, 0.05% BRIJ 35 and 0.01% BSA. The substrate/enzyme mixture was incubated at 30° C. for 10 min. Then 16 µL substrate/enzyme mixture was transferred to 200 µL 1 M NaOH, 1.0% α-naphtol (Sigma, Catalogue #33420) and 0.1% creatine (Sigma, Catalogue #C3630). The substrate/enzyme/color reagent mixture was incubated at 30° C. for 20 min and then $OD_{522\ nm}$ was read. One unit of ALDC activity is defined as the amount of enzyme which produces 1 µmole acetoin per minute under the conditions of the assay

Example 4

Specific Activity of aldB and aldB-T62A Variant

*B. subtilis* transformant containing aldB and aldB_T62A expression cassette was cultured under similar conditions as described in Example 1 and the sterile filtered culture supernatants were analysed for aldB protein and ALDC activity as described in Examples 2 and 3. The results are seen in Table 2. It's clear from this analysis that the secreted aldB-T62A enzyme variant has a significant higher specific activity compared to the wildtype aldB enzyme. The specific activity of aldB was found to be 994.1 U/mg whereas the specific activity of aldB-T62A was 1700.8 U/mg, approximately 1.7 times higher.

TABLE 2

ALDC activity, enzyme protein concentration and calculated specific activity of aldB fermentation samples.

| | | Activity U/mL | Criterion Protein mg/mL | Specific Activity U/mg |
|---|---|---|---|---|
| Sample 1 | aldB | 331.0 | 0.333 | 994.1 |
| Sample 2 | aldB-T62A | 818.5 | 0.481 | 1700.8 |

Example 5

Specific Activity of aldB and aldB-T62A Variant After Addition of Zinc

The activity of aldB has previously been demonstrated to be influenced by the presence of divalent metal ions such as $Zn^{2+}$, $Mn^{2+}$ and $Co^{2+}$ (see International Patent Application Nos. PCT/US16/33028 and PCT/US16/33043). Thus, to study the influence of zinc on the specific activity of aldB and aldB_T62A, all divalent ions were first removed in enzyme samples and then zinc was supplemented to regain activity. Thus enzyme preparations of aldB and aldB_T62A produced in *B. subtilis* as described in Example 4 was desalted using PD10 column prepared as described by the manufacturer and equilibrated with 50 mM MES pH 6.0, 0.6 M NaCl, 0.05% Brij, 0.01% BSA. The desalted samples of aldB and aldB_T62A (approximately 1 mg/ml) were following stripped of divalent ions by incubation with 80 mM EDTA in 0.2× assay buffer (50 mM MES pH 6.0, 0.6 M NaCl, 0.05% Brij, 0.01% BSA) at 37° C. overnight. The EDTA treated material was desalted twice on a PD10 column using demineralised water to remove remaining EDTA. The samples were following incubated with 0 or 0.25 mM $ZnSO_4$ for 1 hr at 55° C. and the ALDC activity and the concentration of AldB protein were determined as described in Examples 2 and 3 (see Table 3).

TABLE 3

Zinc concentration, ALDC activity, enzyme protein concentration and calculated specific activity of desalted aldB samples.

| | | $ZnSO_4$ mM | Activity U/mL | Criterion Protein mg/mL | Specific Activity U/mg |
|---|---|---|---|---|---|
| Sample 1 | aldB | 0 | 16 | 0.423 | 37.8 |
| Sample 2 | aldB | 0.25 | 121 | 0.423 | 286.1 |
| Sample 3 | aldB-T62A | 0 | 3 | 0.244 | 12.3 |
| Sample 4 | aldB-T62A | 0.25 | 137 | 0.244 | 561.5 |

The results clearly show that desalting the aldB samples significantly decreased the specific activity: 37.8 and 12.3 U/mg for aldB and aldB_T62A respectively. Upon incubation with high molar surplus (>8 times) of $ZnSO_4$ for 1 hr at elevated temperature (55 C.°), the specific activity was significantly increased to 286.1 and 561.5 U/mg for aldB and aldB_T62A respectively. The increase in specific activity in zinc was highest for aldB_T62A and the specific activity of aldB_T62A with zinc was approximately 1.9 times higher the corresponding aldB sample. Thus in presence of surplus of a divalent co-factor aldB_T62A showed significant increased specific ALDC activity compared to aldB (wildtype).

Example 6

Specific Activity of aldB and aldB-T62A Variant at Low pH

B. subtilis transformants containing aldB and aldB_T62A expression cassette was cultured under similar conditions as described in Example 1 and the sterile filtered culture supernatants were analysed for aldB protein and ALDC activity as described in Examples 2 and 3. Samples were normalized to 127 U/mL with 50% (v/v) and various $ZnSO_4$ to achieve an addition 25 µM $ZnSO_4$ in the diluted sample. Samples were following diluted to 10 U/mL in a low pH buffer with EDTA (50 mM MES pH 6.0, 0.6 M NaCl, 0.05% Brij, 0.01% BSA, 10 µM EDTA) and incubated using Costar 9017 plates in a PCR machine at 50° C. ALDC activity was followed at the 0, 30, 60 and 90 minutes of incubation. The results are shown in Table 4 together with the calculated specific activity.

TABLE 4

ALDC activity, enzyme protein concentration and calculated specific activity of aldB samples at pH 4.0 and high temperature (50° C.) as function of time.

|  | Time Minutes | Activity U/mL | Criterion Protein mg/mL | Specific Activity U/mg |
|---|---|---|---|---|
| aldB | 0 | 378.8 | 0.257 | 1476.2 |
| aldB | 30 | 380.2 | 0.257 | 1481.8 |
| aldB | 60 | 349.2 | 0.257 | 1360.9 |
| aldB | 90 | 275.4 | 0.257 | 1073.1 |
| aldB-T62A | 0 | 494.5 | 0.149 | 3316.1 |
| aldB-T62A | 30 | 494.1 | 0.149 | 3313.1 |
| aldB-T62A | 60 | 438.0 | 0.149 | 2937.1 |
| aldB-T62A | 90 | 357.1 | 0.149 | 2395.0 |

The results clearly show that the aldB_T62A had a significant higher specific activity (3316.1 U/mg) compared to the aldB samples (1476.2 U/mg) at initiated of low pH incubation. The specific activity of the aldB_T62A was 2.2 times higher aldB normalized with zinc and glycerol. Both samples gradually lost specific activity upon incubation at pH 4.0 (50° C.), however the relative decrease was similar for the two sample over 90 minutes of incubation and approximately 72% of the initial observed specific activity.

Example 9

Reduction in Diacetyl During Beer Fermentation by aldB and aldB-T62A

The objective of this analysis was to test aldB and aldB-T62A variant (acetolactate decarboxylase) ability to reduce development of diacetyl during a 7-day beer fermentation at 14° C.

Pure Malt Brew Analysis 1100 g Munton's Light Malt Extract (Batch XB 35189) extract was dissolved in 3000 mL warm tapwater (45° C.). This slurry was stirred for about 10 min until the liquid was homogeneous and the pH was adjusted to 5.2 with 2.5 M sulphuric acid. To the slurry was added 10 pellets of Bitter hops from Hopfenveredlung, St. Johann: Alpha content of 16.0% (EBC 7.7 0 specific HPLC analysis, Jan. 10, 2013), then split in 500-mL blue-cap bottles and boiled for 1 hour to ensure protein precipitation and avoid potential microbial contamination. The filtered malt extract (wort) was sampled for specific gravity and Free Amino Nitrogen (FAN) determination. The final wort had an initial Specific Gravity of 1048 (12° Plato). Filtered wort (200 g) was added to a 500-mL conical flask (Fermenting Vessel; FV), and then cooled to 13° C. Each conical flask was dosed with 0.5% W34/70 (Weihenstephan) freshly produced yeast (1.0 g yeast per 200 g wort). The enzymes were dosed on similar ALDC activity (0.03 U/mL wort, 8 ALDC Units per 200 g wort). The control fermentation vessel with no enzyme received an amount of deionized water corresponding to the amount of enzyme sample.

The wort samples were fermented in 500-mL conical flasks under standardised laboratory test conditions at 14° C. with gentle agitation at 150 rpm in an orbital incubator. When weight loss was less than 0.25 g over 24 hours, fermentation temperature was decreased to 7° C. Fermentation was stopped after 7 days in total. Samples (10 mL) were taken out for diacetyl analysis two times a day, preferably with 11 to 14 hours in between; at the end of fermentation only 1 sample per day was taken. Yeast was allowed to settle before take-out and each sample was cooled at 10° C. for 10 minutes and then centrifuged at 4000 rpm for 10 minutes at 8° C. to sediment any residual yeast. The supernatant was separated from the yeast sediment and samples for GC analysis were added 0.5 g NaCl per mL of sample. This slurry was transferred to a headspace vial and heat-treated at 65° C. for 30 minutes before analysis for diacetyl and 2,3 pentanedione was carried out by gas chromatography with mass spectrometric detection (GCMS).

Analyses of diacetyl or 2,3-pentanedione were carried out at an Agilent 6890N/5973N GC with CombiPAL headspace autosampler and MSChemStation acquisition and analysis software. The samples were equilibrated at 70° C. for 10 minutes before 500 µL of the gas phase above the sample was injected onto a J&W 122-0763 DB-1701column (60 m×0.25 mmID×1 µm). The injection temperature was 260° C. and the system was operated with a constant helium flow of 2 mL/min. The oven temperature was: 50° C. (2 min), 160° C. (20° C./min), 220° C. (40° C./min), hold 2 min. MS detection were made with 500 µL at a split ratio of 5:1 at selected ions. All samples were run in duplicates and standards were made using tap water with the addition of diacetyl or 2,3-pentanedione.

The concentration of a compound is calculated as $$Compound(mg/L) = \frac{Area}{1000 \times W_s}$$

where,

RF is the response factor of acetic acid

Area is the GC-area of acetic acid $W_s$ is the amount of sample used (in mL)

The limit of diacetyl quantification was determined to 0.016 mg/L and the limit of 2,3-pentanedione quantification was determined to 0.012 mg/L.

To check that addition of ALDC enzymes did not influence the Real Degree of Fermentation (RDF) and the produced alcohol by volume: RDF was measured using an Anton Paar (DMA 5000) following Standard Instruction Brewing, 23.8580-B28 and alcohol by Standard Instruction Brewing, 23.8580-B28.

Results from analysis of wort sample used for all fermented samples.

| Sample type | Extract (° P) | Viscosity at 12° P (mPa · s) | FAN (mg/L) |
|---|---|---|---|
| Wort = Malt Extract | 12.14 | 1.623 | 219 |

The ability to reduce development of VDK during a 7-day fermentation at 14° C. was studied by addition of aldB and aldB-T62A see Table 5.

TABLE 5

ALDC activity, enzyme protein concentration and calculated enzyme concentration in wort

| | ALDC activity U/g | Amount sample for predilution g | Volume predilution mL | Activity in wort U/mL | ALDC protein in wort µg/L |
|---|---|---|---|---|---|
| aldB | 460 | 3.78 | 100 | 0.03 | 75.6 |
| aldB-T62A | 374 | 4.65 | 100 | 0.03 | 48.1 |

Both aldB and aldB-T62A reduced the vicinal diketone (VDK) development during fermentation compared to control. Most important the fermentation time required to reach threshold level of 0.1 mg/mL VDK (sum of diacetyl and 2,3-pentadione) or lower, was observed to be approximately 116 hours for aldB and aldB-T62A whereas it was 140 for the control. Thus, the higher specific activity aldB-T62A enabled comparable VDK reduction using less ALDC protein. The total VDK content at the end of fermentation is given in Table 6.

TABLE 6

Total VDK in mg/L after 97, 116 and 140 hrs of fermentation with the inclusion of aldB, aldB-T62A or no enzyme control.

| | Vicinal diketone (VDK) mg/L | | |
|---|---|---|---|
| | Time: 97 hrs | Time: 116 hrs | Time 140 hrs |
| Control | 0.245 | 0.112 | 0.078 |
| AldB | 0.148 | 0.070 | 0.078 |
| AldB-762A | 0.134 | 0.071 | 0.063 |

The invention claimed is:

1. A recombinant polypeptide having acetolactate decarboxylase (ALDC) activity comprising
   (i) at least 95% amino acid identity to amino acid sequence of SEQ ID NO: 3 and wherein the polypeptide comprises at least one amino acid substitution at position 62 with reference to the position numbering of the sequence shown in SEQ ID NO: 3 or
   (ii) a functional fragment of (i) having a specific activity greater than or equal to the specific activity of (i).

2. The recombinant polypeptide of claim 1 having at least 99% amino acid identity to amino acid sequence of SEQ ID NO: 3.

3. The recombinant polypeptide of claim 2 wherein the amino acid substitution is T62A.

4. The recombinant polypeptide of claim 3 having the amino acid sequence of SEQ ID NO: 8.

5. A composition comprising a recombinant polypeptide having acetolactate decarboxylase (ALDC) activity comprising
   (i) at least 95% amino acid identity to amino acid sequence of SEQ ID NO: 3 and wherein the polypeptide comprises at least one amino acid substitution at position 62 with reference to the position numbering of the sequence shown in SEQ ID NO: 3 or
   (ii) a functional fragment of (i) having a specific activity greater than or equal to the specific activity of (i) and zinc at concentration of about 1 µM to about 200 mM.

6. The composition of claim 5, wherein the zinc is present at a concentration of about 10 µM to about 150 mM, or about 20 µM to about 120 mM, or about 25 µM to about 100 mM, or about 25 µM to about 50 mM, or about 25 µM to about 20 mM, or about 25 µM to about 50 µM, or about 100 µM to about 20 mM, or about 250 µM to about 20 mM, or about 500 µM to about 20 mM, or about 1 mM to about 20 mM, or about 1 mM to about 10 mM, or about 1 mM to about 5 mM.

7. The composition of claim 5 wherein the molar ratio of zinc to the recombinant polypeptide is
   (i) higher than 1; or
   (ii) 2:1 or higher; or
   (iii) 10:1 or higher; or
   (iv) 20:1 or higher; or
   (v) 30:1 or higher; or
   (vi) 60:1 or higher.

8. The composition of claim 5, wherein the recombinant polypeptide having acetolactate decarboxylase activity is treated with glutaraldehyde.

9. The composition of claim 8, wherein the recombinant polypeptide having acetolactate decarboxylase activity is treated with glutaraldehyde is at a concentration corresponding to about 0.1 grams to about 5 grams of glutaraldehyde per gram of recombinant polypeptide having acetolactate decarboxylase activity.

10. The composition of claim 5, wherein the activity of said recombinant polypeptide having acetolactate decarboxylase activity is in the range of 950 to 3500 Units per mg of protein.

11. The composition of claim 5 further comprising at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endoglucanase and related beta-glucan hydrolytic accessory enzymes, xylanase, arabinofuranosidase, ferulic acid esterase, xylan acetyl esterase and protease.

12. The composition of claim 5, wherein the recombinant polypeptide having acetolactate decarboxylase activity is derived from an acetolactate decarboxylase from *Bacillus brevis* or *Bacillus licheniformis*.

13. A method for increasing the activity and/or stability of a recombinant polypeptide having acetolactate decarboxylase (ALDC) activity comprising
   (i) at least 95% amino acid identity to amino acid sequence of SEQ ID NO: 3 and wherein the polypeptide comprises at least one amino acid substitution at position 62 with reference to the position numbering of the sequence shown in SEQ ID NO: 3 or
   (ii) a functional fragment of (i) having a specific activity greater than or equal to the specific activity of (i) wherein said method comprises the step of adding zinc to a composition comprising the recombinant polypeptide so that said zinc is present in said composition at a concentration of about 1 µM to about 200 mM.

14. The method of claim 13, wherein said zinc is added at a concentration of 1 µM to about 5 mM.

15. A cultivation media for a recombinant host cell capable of producing a recombinant polypeptide having acetolactate decarboxylase (ALDC) activity comprising
   (i) at least 95% amino acid identity to amino acid sequence of SEQ ID NO: 3 and wherein the polypeptide comprises at least one amino acid substitution at position 62 with reference to the position numbering of the sequence shown in SEQ ID NO: 3 or
   (ii) a functional fragment of (i) having a specific activity greater than or equal to the specific activity of (i) comprising zinc at a concentration of about 1 µM to about 1 mM.

16. The cultivation media of claim 15, comprising zinc at concentration of about 60 µM to about 150 µM.

17. A beer, wine, cider, perry or sake fermentation media or maturation media comprising a composition comprising
   a) a recombinant polypeptide having acetolactate decarboxylase (ALDC) activity comprising
      (i) at least 95% amino acid identity to amino acid sequence of SEQ ID NO: 3 and wherein the polypeptide comprises at least one amino acid substitution at position 62 with reference to the position numbering of the sequence shown in SEQ ID NO: 3 or
      (ii) a functional fragment of (i) having a specific activity greater than or equal to the specific activity of (i), and;
   b) zinc; wherein said composition comprises zinc at a concentration of about 1 µM to about 200 mM.

18. The beer, wine, cider, perry or sake fermentation media of or maturation media of claim 17, wherein the activity of said recombinant polypeptide having acetolactate decarboxylase activity is in the range of 1000 to 3500 Units per mg of protein.

19. The beer, wine, cider, perry or sake fermentation media or maturation media of claim 18, further comprising at least one additional enzyme or enzyme derivative selected from the group consisting of acetolactate reductoisomerases, acetolactate isomerases, amylase, glucoamylase, hemicellulase, cellulase, glucanase, pullulanase, isoamylase, endoglucanase and related beta-glucan hydrolytic accessory enzymes, xylanase, xylanase accessory enzymes (for example, arabinofuranosidase, ferulic acid esterase, and xylan acetyl esterase) and protease.

20. A method for beer, wine, cider, perry or sake production comprising adding a composition comprising a recombinant polypeptide having acetolactate decarboxylase (ALDC) activity comprising (i) at least 95% amino acid identity to amino acid sequence of SEQ ID NO: 3 and wherein the polypeptide comprises at least one amino acid substitution at position 62 with reference to the position numbering of the sequence shown in SEQ ID NO: 3 or (ii) a functional fragment of (i) having a specific activity greater than or equal to the specific activity of (i) and zinc to a media suitable for the beer, wine, cider, perry or sake production.

21. The method of claim 20 wherein:
   (i) zinc is present in the composition at a concentration of about 1 mM to about 5 mM; or
   (ii) the molar ratio of zinc to the recombinant polypeptide having acetolactate decarboxylase activity in the composition is higher than 1; or 2:1 or higher; or 10:1 or higher; or 20:1 or higher; or 30:1 or higher; or 60:1 or higher.

* * * * *